US012629247B2

(12) United States Patent
Irby et al.

(10) Patent No.: US 12,629,247 B2
(45) Date of Patent: May 19, 2026

(54) ADJUSTABLE INTRAOCULAR LENSES AND METHODS OF POST OPERATIVELY ADJUSTING INTRAOCULAR LENSES

(71) Applicant: Alcon Inc., Fribourg (CH)

(72) Inventors: Sean Michael Irby, San Francisco, CA (US); Shivam Agarwal, Sunnyvale, CA (US)

(73) Assignee: Alcon Inc., Fribourg (CH)

( * ) Notice: Subject to any disclaimer, the term of this patent is extended or adjusted under 35 U.S.C. 154(b) by 534 days.

(21) Appl. No.: 18/153,951

(22) Filed: Jan. 12, 2023

(65) Prior Publication Data

US 2023/0240836 A1     Aug. 3, 2023

Related U.S. Application Data

(60) Provisional application No. 63/267,376, filed on Jan. 31, 2022.

(51) Int. Cl.
A61F 2/16          (2006.01)
(52) U.S. Cl.
CPC .. A61F 2/1635 (2013.01); *A61F 2002/16901* (2015.04); *A61F 2210/008* (2013.01); *A61F 2250/0001* (2013.01); *A61F 2250/0097* (2013.01)
(58) Field of Classification Search
CPC ................ A61F 2/1613; A61F 2/1616–2/1659
See application file for complete search history.

(56) References Cited

U.S. PATENT DOCUMENTS

| | | | |
|---|---|---|---|
| 3,278,654 A | 10/1966 | Grandperret |
| 3,846,013 A | 11/1974 | Cohen |
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,258,311 A | 3/1981 | Tokuda et al. |
| 4,304,895 A | 12/1981 | Loshaek |
| 4,373,218 A | 2/1983 | Schachar |

(Continued)

FOREIGN PATENT DOCUMENTS

| | | | |
|---|---|---|---|
| CA | 2903598 | 7/2008 | |
| CA | 2507694 C * | 7/2012 | ........... A61F 2/1616 |

(Continued)

OTHER PUBLICATIONS

Baughman et al. "Negative poisson's ratios for extreme states fo matter," *Science*, vol. 288, pp. 2018-2022, Jun. 16, 2000.

(Continued)

*Primary Examiner* — Alvin J Stewart
(74) *Attorney, Agent, or Firm* — Levine Bagade Han LLP

(57) ABSTRACT

Disclosed are adjustable intraocular lenses and methods of adjusting intraocular lenses post-operatively. In one embodiment, an adjustable accommodating intraocular lens comprises an optic portion and at least one haptic. At least part of the haptic can be made in part of a composite material comprising an energy absorbing constituent and a plurality of shrinkable and/or burstable microspheres. At least one of a base power of the optic portion can be configured to change in response to an external energy directed at the composite material.

20 Claims, 6 Drawing Sheets

(56)  References Cited

U.S. PATENT DOCUMENTS

| | | | |
|---|---|---|---|
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turley |
| 4,902,293 A | 2/1990 | Feaster |
| 4,913,536 A | 4/1990 | Barnea |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,169,920 A | 12/1992 | Okawa |
| 5,171,266 A | 12/1992 | Wiley et al. |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,217,491 A | 6/1993 | Vanderbilt |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,426,166 A | 6/1995 | Usifer et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,483,305 A | 1/1996 | Kohayakawa |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,567,365 A | 10/1996 | Weinschenk, III et al. |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,676,669 A | 10/1997 | Colvard |
| 5,693,095 A | 12/1997 | Freeman et al. |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,800,533 A | 9/1998 | Eggleston et al. |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,968,095 A | 10/1999 | Norrby |
| 5,984,962 A | 11/1999 | Anello et al. |
| 6,013,101 A | 1/2000 | Israel |
| 6,015,842 A | 1/2000 | LeBoeuf et al. |
| 6,045,745 A | 4/2000 | Reno |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skotton |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,528,602 B1 | 3/2003 | Freeman et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |

(56)    References Cited

U.S. PATENT DOCUMENTS

| | | |
|---|---|---|
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,438,723 B2 | 10/2008 | Esch |
| 7,485,144 B2 | 2/2009 | Esch |
| 7,494,505 B2 | 2/2009 | Kappelhof et al. |
| 7,637,947 B2 | 12/2009 | Smith et al. |
| 7,763,069 B2 | 7/2010 | Brady et al. |
| 7,776,088 B2 | 8/2010 | Shadduck |
| 7,988,292 B2 | 8/2011 | Neal et al. |
| 8,048,155 B2 | 11/2011 | Shadduck |
| 8,158,712 B2 | 4/2012 | Your |
| 8,162,927 B2 | 4/2012 | Peyman |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,662,663 B2 | 3/2014 | Matsushita et al. |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,044,317 B2 | 6/2015 | Hildebrand et al. |
| 9,277,987 B2 | 3/2016 | Smiley et al. |
| 9,456,895 B2 | 10/2016 | Shadduck |
| 9,693,858 B2 | 7/2017 | Hildebrand et al. |
| 9,855,139 B2 | 1/2018 | Matthews et al. |
| 10,042,183 B2 | 8/2018 | Goodenough et al. |
| 10,076,858 B2 | 9/2018 | Gerardi et al. |
| 10,159,566 B2 | 12/2018 | Hadba et al. |
| 10,195,020 B2 | 2/2019 | Matthews |
| 10,299,913 B2 | 5/2019 | Smiley et al. |
| 10,350,060 B2 | 7/2019 | Smiley et al. |
| 10,368,979 B2 * | 8/2019 | Scholl .................. A61F 2/1635 |
| 10,433,949 B2 | 10/2019 | Smiley et al. |
| 10,433,950 B2 | 10/2019 | Shadduck |
| 10,534,113 B2 | 1/2020 | Shadduck |
| 10,595,989 B2 | 3/2020 | Hildebrand et al. |
| 11,426,270 B2 | 8/2022 | Hildebrand et al. |
| 11,471,272 B2 * | 10/2022 | Smiley .................... A61L 27/54 |
| 11,660,182 B2 * | 5/2023 | Smiley .................. A61F 2/1659 |
| | | 623/6.13 |
| 12,167,959 B2 | 12/2024 | Smiley et al. |
| 12,245,930 B2 | 3/2025 | Bor |
| 12,370,040 B2 | 7/2025 | Smiley |
| 12,376,957 B2 * | 8/2025 | Argento ............... A61F 2/1645 |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0016629 A1 | 2/2002 | Sandstedt et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0188351 A1 | 12/2002 | Laguette |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 * | 3/2003 | Shadduck ............. A61F 2/1635 |
| | | 623/6.13 |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0147046 A1 | 8/2003 | Shadduck |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0234456 A1 | 12/2003 | Deryke et al. |
| 2003/0236376 A1 | 12/2003 | Kindt-Larsen et al. |
| 2004/0001180 A1 | 1/2004 | Epstein |
| 2004/0006386 A1 | 1/2004 | Valint, Jr. et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0100704 A1 | 5/2004 | Shadduck |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |

(56) References Cited

U.S. PATENT DOCUMENTS

| | | |
|---|---|---|
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0230203 A1 | 11/2004 | Yaguchi |
| 2005/0021139 A1 | 1/2005 | Shadduck |
| 2005/0090612 A1 | 4/2005 | Soane et al. |
| 2005/0113911 A1 | 5/2005 | Peyman |
| 2005/0119740 A1 | 6/2005 | Esch et al. |
| 2005/0125000 A1 | 6/2005 | Tourrette et al. |
| 2005/0131535 A1 | 6/2005 | Woods |
| 2005/0146685 A1 | 7/2005 | Hanaki et al. |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0061729 A1 | 3/2006 | Shadduck |
| 2006/0069433 A1 | 3/2006 | Nun |
| 2006/0084949 A1 | 4/2006 | Peyman |
| 2006/0158611 A1 | 7/2006 | Piers et al. |
| 2006/0246112 A1 | 11/2006 | Snyder et al. |
| 2006/0253196 A1 | 11/2006 | Woods |
| 2007/0010880 A1 | 1/2007 | Esch |
| 2007/0035049 A1 | 2/2007 | Bruce et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0124919 A1 | 6/2007 | Probst |
| 2007/0203578 A1 | 8/2007 | Scholl et al. |
| 2007/0213817 A1 | 9/2007 | Esch et al. |
| 2007/0260308 A1 | 11/2007 | Tran |
| 2007/0299487 A1 | 12/2007 | Shadduck |
| 2008/0015689 A1 | 1/2008 | Esch et al. |
| 2008/0023137 A1 | 1/2008 | Jiang et al. |
| 2008/0046074 A1 | 2/2008 | Smith et al. |
| 2008/0046075 A1 | 2/2008 | Esch et al. |
| 2008/0306587 A1 | 12/2008 | Your |
| 2009/0005865 A1* | 1/2009 | Smiley ................. A61F 2/1635 |
| | | 623/6.13 |
| 2009/0030425 A1 | 1/2009 | Smiley et al. |
| 2009/0079940 A1 | 3/2009 | Dai et al. |
| 2009/0149952 A1 | 6/2009 | Shadduck |
| 2009/0155371 A1 | 6/2009 | Sojka et al. |
| 2009/0292355 A1 | 11/2009 | Boyd et al. |
| 2009/0312836 A1 | 12/2009 | Pinchuk et al. |
| 2010/0016965 A1 | 1/2010 | Hong et al. |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0027766 A1 | 2/2011 | Yoo et al. |
| 2011/0052020 A1 | 3/2011 | Hildebrand et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2012/0022547 A1 | 1/2012 | Hildebrand et al. |
| 2012/0078361 A1 | 3/2012 | Shadduck |
| 2012/0226351 A1 | 9/2012 | Peyman |
| 2012/0245591 A1 | 9/2012 | Matthews |
| 2013/0060331 A1 | 3/2013 | Shadduck |
| 2013/0103146 A1 | 4/2013 | Smiley et al. |
| 2013/0131794 A1 | 5/2013 | Smiley et al. |
| 2013/0176530 A1 | 7/2013 | Goodenough et al. |
| 2013/0250239 A1 | 9/2013 | Hildebrand et al. |
| 2013/0268070 A1 | 10/2013 | Esch et al. |
| 2014/0249625 A1 | 9/2014 | Shadduck |
| 2014/0293217 A1 | 10/2014 | Ogaya et al. |
| 2015/0057642 A1 | 2/2015 | Zickler et al. |
| 2015/0087743 A1 | 3/2015 | Anvar et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0038278 A1 | 2/2016 | Matthews |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2016/0263781 A1 | 9/2016 | Gerardi et al. |
| 2017/0020662 A1 | 1/2017 | Shadduck |
| 2017/0049561 A1 | 2/2017 | Smiley et al. |
| 2017/0079773 A1 | 3/2017 | Matthews et al. |
| 2017/0281334 A1 | 10/2017 | Zhao |
| 2017/0290658 A1 | 10/2017 | Hildebrand et al. |
| 2018/0085213 A1 | 3/2018 | Hadba et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161150 A1 | 6/2018 | Hadad et al. |
| 2018/0177589 A1 | 6/2018 | Argento et al. |
| 2018/0200112 A1 | 7/2018 | Krampert et al. |
| 2018/0256315 A1 | 9/2018 | Hildebrand et al. |
| 2019/0038401 A1 | 2/2019 | Reich et al. |
| 2019/0053892 A1 | 2/2019 | Siney et al. |
| 2019/0076243 A1 | 3/2019 | Hadba et al. |
| 2019/0361231 A1 | 11/2019 | Kurz |
| 2019/0366660 A1 | 12/2019 | Ge et al. |
| 2019/0374333 A1 | 12/2019 | Shadduck |
| 2020/0070453 A1 | 3/2020 | Piotrowski et al. |
| 2020/0146813 A1* | 5/2020 | Argento ............... A61F 2/1635 |
| 2020/0315848 A1 | 10/2020 | Rosen |
| 2020/0332085 A1 | 10/2020 | Ebe et al. |
| 2020/0337833 A1 | 10/2020 | Green |
| 2020/0405541 A1 | 12/2020 | Raksi |
| 2021/0100649 A1* | 4/2021 | Smiley .................. A61F 2/1605 |
| 2021/0100650 A1* | 4/2021 | Smiley .................. A61F 2/1624 |
| 2021/0186320 A1 | 6/2021 | Copland |
| 2021/0221068 A1* | 7/2021 | Schramm ............... B22F 10/85 |
| 2021/0251744 A1* | 8/2021 | Goldshleger ........... A61L 27/18 |
| 2021/0291469 A1 | 9/2021 | Zheng et al. |
| 2022/0227082 A1 | 7/2022 | Körner et al. |
| 2022/0313080 A1 | 10/2022 | Hernandez et al. |
| 2022/0409363 A1 | 12/2022 | Smiley |
| 2023/0191730 A1 | 6/2023 | Walz et al. |
| 2023/0200976 A1* | 6/2023 | Salahieh .............. B29D 11/023 |
| | | 623/6.22 |
| 2023/0248509 A1 | 8/2023 | Smiley et al. |
| 2024/0148554 A1* | 5/2024 | Paliwal ............... A61F 9/00834 |
| 2024/0325139 A1 | 10/2024 | Walz et al. |
| 2024/0325140 A1 | 10/2024 | Smiley et al. |
| 2025/0000642 A1 | 1/2025 | Bor |
| 2025/0057644 A1 | 2/2025 | Smiley et al. |
| 2025/0107886 A1* | 4/2025 | Leroy ................. A61F 9/00834 |
| 2025/0177121 A1 | 6/2025 | Bor |

FOREIGN PATENT DOCUMENTS

| | | |
|---|---|---|
| CN | 1283974 | 2/2001 |
| CN | 1367667 | 9/2002 |
| CN | 1378440 | 11/2002 |
| CN | 1384727 | 12/2002 |
| CN | 101277659 | 10/2008 |
| CN | 104244867 | 11/2017 |
| EP | 0898972 | 3/1999 |
| EP | 1358858 | 11/2003 |
| FR | 2655841 | 6/1991 |
| FR | 2784575 | 12/2000 |
| JP | H05(1993)-171056 | 7/1993 |
| JP | 07-044938 | 5/1995 |
| JP | 08-501715 | 2/1996 |
| JP | 08-224295 | 9/1996 |
| JP | 09-294754 | 11/1997 |
| JP | 10-206609 | 8/1998 |
| JP | 11-047168 | 2/1999 |
| JP | 1999-047168 | 2/1999 |
| JP | 11-056998 | 3/1999 |
| JP | 11-169391 | 6/1999 |
| JP | 11-276509 | 10/1999 |
| JP | 11-332903 | 12/1999 |
| JP | 2000-250203 | 9/2000 |
| JP | 2001-502592 | 2/2001 |

(56) References Cited

FOREIGN PATENT DOCUMENTS

| | | |
|---|---|---|
| JP | 2003-144387 | 5/2003 |
| JP | 2003-524503 | 8/2003 |
| JP | 2003-530978 | 10/2003 |
| JP | 2006-523130 | 10/2006 |
| JP | 2007-513715 | 5/2007 |
| JP | 2007-516794 | 6/2007 |
| JP | 2007-518447 | 7/2007 |
| JP | 2010-095719 | 4/2010 |
| JP | 2010-518948 | 6/2010 |
| JP | 2010-534520 | 11/2010 |
| JP | 2016-138050 | 8/2016 |
| JP | 2017-148614 | 8/2017 |
| JP | 2018-047096 | 3/2018 |
| SU | 1810052 | 4/1993 |
| WO | WO 1992/010150 | 6/1992 |
| WO | WO 1995/002378 | 1/1995 |
| WO | WO 1997/006751 | 2/1997 |
| WO | WO 1999/029265 | 6/1999 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2004/081613 | 9/2004 |
| WO | WO 2005/018504 | 3/2005 |
| WO | WO 2005/084588 | 9/2005 |
| WO | WO 2006/039269 | 4/2006 |
| WO | WO 2008/102582 | 8/2008 |
| WO | WO 2009/015234 | 1/2009 |
| WO | WO 2010/125596 | 11/2010 |
| WO | WO 2018/222558 | 12/2018 |
| WO | WO 2018/227014 | 12/2018 |
| WO | WO 2021/067574 | 4/2021 |
| WO | WO 2021/067579 | 4/2021 |
| WO | WO 2022/216451 | 10/2022 |
| WO | WO 2023/122490 | 6/2023 |
| WO | WO 2023/147224 | 8/2023 |
| WO | WO 2024/102536 | 5/2024 |
| WO | WO 2024/206250 | 10/2024 |
| WO | WO 2024/206251 | 10/2024 |
| WO | WO 2025/006182 | 1/2025 |
| WO | WO 2025/178731 | 8/2025 |

OTHER PUBLICATIONS

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

Dubbelman et al. "The Thickness of the Aging Human Lens Obtained from Corrected Scheimpflug Images," *Optometry & Vision Science*; vol. 78; iss. 6; pp. 411-416; Jun. 2001.

European Patent Application No. 04718213.4 filed Mar. 6, 2004 in the name of PowerVision, Inc., Office Action mailed Feb. 8, 2008.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

International Patent Application No. PCT/US2004/006958 filed Mar. 6, 2004 in the name of PowerVision, Inc., International Search Report mailed Nov. 5, 2004.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No. contractile obligations," *Nature*, vol. 358, pp. 713-714, Dec. 31, 1992.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wyant et al.; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

7.7 Solubility, Chemistry for Allied Health, https://chem.libretexts.org/Bookshelves/Introductory_Chemistry/Chemistry_for_Allied_Health_(Soult)/07%3A_Solids_Liquids_and_Gases/7.07%3A_Solubility, 6 pages, 2019.

Sun, M. et al. "Intraocular lens alignment from an en face optical coherence tomography image Purkinje-like method", *Optical Engi-*

(56) References Cited

OTHER PUBLICATIONS

*neering, Society of Photo-Optical Instrumentation Engineers*, vol. 51, No. 6, pp. 061704-1 to 061704-9, Jun. 1, 2014.
Wikipedia's Article on O-ring, https://web.archive.org/web/20211022014544/https://en.wikipedia.org/wiki/O-ring, 10 pages, 2021.

* cited by examiner

ADJUSTABLE INTRAOCULAR LENSES AND METHODS OF POST OPERATIVELY ADJUSTING INTRAOCULAR LENSES

CROSS-REFERENCE TO RELATED APPLICATION

This application claims priority to U.S. Patent Application No. 63/267,376 filed on Jan. 31, 2022, the content of which is incorporated herein by reference in its entirety.

TECHNICAL FIELD

The present disclosure relates generally to the field of intraocular lenses, and, more specifically, to adjustable intraocular lenses and methods of adjusting intraocular lenses.

BACKGROUND

A cataract is a condition involving the clouding over of the normally clear lens of a patient's eye. Cataracts occur as a result of aging, hereditary factors, trauma, inflammation, metabolic disorders, or exposure to radiation. Age-related cataract is the most common type of cataracts. In treating a cataract, the surgeon removes the crystalline lens matrix from the patient's lens capsule and replaces it with an intraocular lens (IOL). Traditional IOLs provide one or more selected focal lengths that allow the patient to have distance vision. However, after cataract surgery, patients with traditional IOLs often require glasses or other corrective eyewear for certain activities since the eye can no longer undertake accommodation (or change its optical power) to maintain a clear image of an object or focus on an object as its distance varies.

Newer IOLs such as accommodating IOLs, allow the eye to regain at least some focusing ability. Accommodating IOLs (AIOLs) use forces available in the eye to change some portion of the optical system in order to refocus the eye on distant or near targets.

With all IOLs, including both AIOLs and non-accommodating IOLs, there may be a need to adjust such lenses post-operatively or after implantation within the eye of a patient.

Therefore, a solution is needed which allows for post-implant adjustment of IOLs without having to undergo additional surgery. Such a solution should allow for effective negative tuning of the optical power of the IOL as well as positive tuning.

SUMMARY

Disclosed herein are adjustable intraocular lenses and methods of adjusting intraocular lenses post-operatively. In one embodiment, an intraocular lens is disclosed comprising an optic portion and one or more haptics coupled to the optic portion. At least one of the haptics can comprise a composite material. The composite material can comprise an energy absorbing constituent and a plurality of shrinkable and/or burstable microspheres. A base power of the optic portion can be configured to change in response to an external energy directed at the composite material.

Each of the shrinkable and/or burstable microspheres can comprise an inner phase and one or more vacuum voids contained within a thermoplastic shell. The inner phase can be configured to undergo a phase change from a vapor into a liquid phase at a temperature below a boiling point of the inner phase. The vacuum voids can be formed when the inner phase condenses into the liquid phase within the thermoplastic shell.

In some embodiments, the inner phase can be water. In other embodiments, the inner phase can be ethylene glycol.

In some embodiments, the thermoplastic shell can be made in part of polyacrylonitrile. In other embodiments, the thermoplastic shell can be made in part of polystyrene. The thermoplastic shell can also be made in part of poly(methyl methacrylate).

The thermoplastic shell can be configured to soften at a temperature above a glass transition temperature of the thermoplastic shell. The thermoplastic shell can be configured to soften and collapse or disintegrate/rupture in response to the external energy directed at the composite material. In the case of the shrinkable microspheres, the thermoplastic shell can re-form around the inner phase.

In some embodiments, a diameter of at least one of the shrinkable microspheres can be configured to decrease by about one-half in response to the external energy directed at the composite material. The shrinkable microspheres can comprise between about 5% to about 25% by weight of the composite material.

The energy absorbing constituent can be an energy absorbing colorant. For example, the energy absorbing colorant can be a dye. As a more specific example, the dye can be an azo dye. The energy absorbing colorant can also be a pigment. For example, the pigment can be graphitized carbon black. The energy absorbing constituent can be configured to transfer thermal energy to the plurality of shrinkable and/or burstable microspheres in response to the external energy directed at the composite material.

At least one of the optic portion and the one or more haptics can be made in part of a cross-linked copolymer comprising a copolymer blend. The composite material can be made in part of the copolymer blend. In some embodiments, the copolymer blend can comprise an alkyl acrylate, a fluoro-alkyl acrylate, and a phenyl-alkyl acrylate. The composite material can further comprise at least one of reactive acrylic monomer diluents, a photoinitiator, and a thermal initiator.

In some embodiments, the external energy can be light energy. For example, the light energy can be a laser light.

The change in the base power can be a persistent change. The base power of the optic portion can be configured to decrease in response to the external energy directed at the composite material.

The optic portion can comprise a fluid-filled optic chamber and at least one of the haptics can comprise a fluid-filled haptic fluid lumen in fluid communication with the optic fluid chamber. The base power of the intraocular lens can be configured to decrease in response to fluid displacement between the optic fluid chamber and the haptic fluid lumen as a result of the external energy directed at the composite material. The base power can be configured to change in response to a change in a volume of the haptic fluid lumen as a result of the external energy directed at the composite material.

The composite material can be located partly within a channel formed along a radially inner wall of at least one of the haptics. The channel can be part of and in fluid communication with the haptic fluid lumen. A volume of the haptic fluid lumen can be configured to increase in response to the external energy directed at the composite material.

The composite material can be configured as a mass extending into the channel. The volume of the mass can be configured to decrease in response to the external energy directed at the composite material. The volume of the haptic fluid lumen can be configured to increase in response to the decrease in the volume of the mass.

Also disclosed is a method of adjusting an intraocular lens. The method can comprise adjusting a base power of the intraocular lens by directing an external energy at a composite material within at least one haptic of the intraocular lens. The composite material can comprise an energy absorbing constituent and a plurality of shrinkable and/or burstable microspheres. The base power of the intraocular lens can be adjusted when the intraocular lens is implanted within an eye of a subject.

The step of adjusting the base power of the intraocular lens can comprise directing the external energy at the composite material to energize the energy absorbing constituent to cause thermal energy to be transferred to the plurality of shrinkable and/or burstable microspheres.

Each of the shrinkable microspheres and burstable microspheres can comprise an inner phase and one or more vacuum voids contained within a thermoplastic shell. Directing the external energy at the composite material can shrink the shrinkable microspheres or burst the burstable microspheres.

The thermoplastic shell can be configured to soften at a temperature above a glass transition temperature of the thermoplastic shell. A diameter of at least one of the shrinkable microspheres can be configured to decrease by about one-half in response to the external energy directed at the composite material.

In some embodiments, the intraocular lens can comprise an optic portion comprising a fluid-filled optic chamber. The at least one haptic can comprise a fluid-filled haptic fluid lumen in fluid communication with the optic fluid chamber. The step of directing the external energy at the composite material can cause fluid displacement between the optic fluid chamber and the haptic fluid lumen. The base power of the intraocular lens can be configured to decrease in response to the fluid displacement between the optic fluid chamber and the haptic fluid lumen.

The composite material can be located partly within a channel formed along a radially inner wall of at least one of the haptics. The channel can be in fluid communication with the haptic fluid lumen. A volume of the haptic fluid lumen can be configured to increase in response to the external energy directed at the composite material.

The composite material can be configured as a mass extending into the channel. The volume of the mass can be configured to decrease in response to the external energy directed at the composite material. The volume of the haptic fluid lumen can be configured to increase in response to the decrease in the volume of the mass. In some embodiments, the external energy can be light energy.

Further disclosed is an intraocular lens comprising an optic portion and at least one haptic coupled to the optic portion. The at least one haptic can comprise a first composite material. The first composite material can comprise an energy absorbing constituent and a plurality of shrinkable and/or burstable microspheres. In some embodiments, a portion of the at least one haptic can be made in part of a second composite material comprising the energy absorbing constituent and a plurality of expandable microspheres. A base power of the optic portion can be configured to decrease in response to an external energy directed at the first composite material and the base power of the optic portion can be configured to increase in response to the external energy directed at the second composite material.

Each of the shrinkable microspheres and burstable microspheres of the first composite material can comprise an inner phase and one or more vacuum voids contained within a first thermoplastic shell. The inner phase can be configured to undergo a phase change from a vapor into a liquid phase at a temperature below a boiling point of the inner phase. The vacuum voids can be formed when the inner phase condenses into the liquid phase within the first thermoplastic shell.

Each of the expandable microspheres of the second composite material can comprise a blowing agent contained within a second thermoplastic shell.

The optic portion can comprise a fluid-filled optic fluid chamber. The at least one haptic can comprise a fluid-filled haptic fluid lumen in fluid communication with the optic fluid chamber. Directing the external energy at the first composite material can cause fluid to be displaced from the optic fluid chamber into the haptic fluid lumen. The base power can be configured to decrease in response to the fluid displacement between the optic fluid chamber and the haptic fluid lumen.

In some embodiments, the first composite material can be located partly within a channel formed along a radially inner wall of the at least one haptic. The channel can be in fluid communication with the haptic fluid lumen. A volume of the haptic fluid lumen can be configured to increase in response to the external energy directed at the first composite material.

The first composite material can be configured as a mass extending into the channel. The volume of the mass can be configured to decrease in response to the external energy directed at the first composite material. The volume of the haptic fluid lumen can be configured to increase in response to the decrease in the volume of the mass.

At least part of a radially inner wall of the at least one haptic can be made of the second composite material. A portion of the second composite material can be in fluid communication with the channel.

A portion of the second composite material can be configured to expand into the channel in response to the external energy directed at the second composite material. In some embodiments, the external energy can be light energy.

Also disclosed is a size-adjustable ophthalmic material, comprising an energy absorbing constituent and a plurality of at least one of shrinkable microspheres and burstable microspheres. A size of the ophthalmic material can be configured to change in response to an external energy directed at the ophthalmic material.

Each of the shrinkable microspheres and burstable microspheres can comprise an inner phase and one or more vacuum voids contained within a thermoplastic shell. The inner phase can be configured to undergo a phase change from a vapor into a liquid phase at a temperature below a boiling point of the inner phase. The vacuum voids can be formed when the inner phase condenses into the liquid phase within the thermoplastic shell.

In some embodiments, the inner phase can be water. In other embodiments, the inner phase can be ethylene glycol.

The thermoplastic shell can be made in part of polyacrylonitrile. The thermoplastic shell can also be made in part of polystyrene. The thermoplastic shell can also be made in part of poly(methyl methacrylate).

The thermoplastic shell can be configured to soften at a temperature above a glass transition temperature of the thermoplastic shell. The thermoplastic shell can be configured to soften and collapse in response to the external energy directed at the ophthalmic material and re-form around the inner phase.

A diameter of at least one of the shrinkable microspheres can be configured to decrease by about one-half in response to the external energy directed at the ophthalmic material. At least one of the shrinkable microspheres and the burstable microspheres can comprise between about 5% to about 25% by weight of the ophthalmic material.

The energy absorbing constituent can be an energy absorbing colorant. For example, the energy absorbing colorant can be a dye. As a more specific example, the dye can be an azo dye.

The energy absorbing colorant can be a pigment. For example, the pigment can be graphitized carbon black.

In some embodiments, the external energy can be light energy. For example, the light energy can be a laser light.

The energy absorbing constituent can be configured to transfer thermal energy to the plurality of the at least one of the shrinkable microspheres and the burstable microspheres in response to the external energy directed at the ophthalmic material.

In some embodiments, the ophthalmic material can comprise only shrinkable microspheres. In other embodiments, the ophthalmic material can comprise only burstable microspheres.

DETAILED DESCRIPTION

Figure 1A:
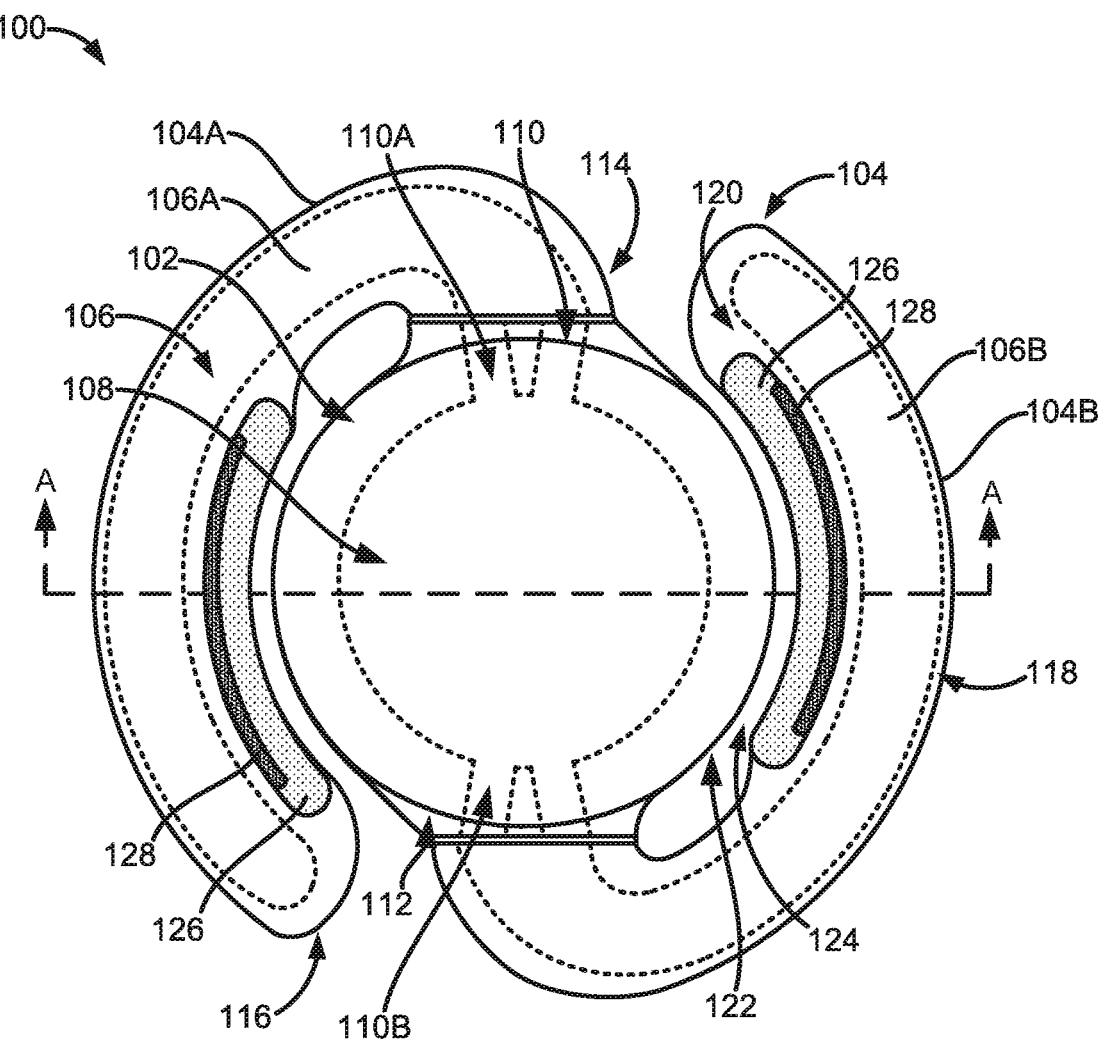
FIG. 1A illustrates a top plan view of one embodiment of an IOL.

FIG. 1A illustrates a top plan view of one embodiment of an adjustable intraocular lens (IOL) 100. For example, the adjustable IOL can be an adjustable accommodating IOL (AIOL). Examples of AIOLs are discussed in the following U.S. patent publications: U.S. Pat. Pub. No. 2021/0100652; U.S. Pat. Pub. No. 2021/0100650; U.S. Pat. Pub. No. 2020/0337833; U.S. Pat. Pub. No. 2018/0256315; U.S. Pat. Pub. No. 2018/0153682; and U.S. Pat. Pub. No. 2017/0049561 and in the following issued U.S. patents: U.S. Pat. Nos. 10,299,913; 10,195,020; and 8,968,396, the contents of which are incorporated herein by reference in their entireties. In other embodiments not shown in the figures, the adjustable IOL 100 can also be a non-accommodating or static-focus adjustable IOL.

The IOL 100 can be implanted within a subject to correct for defocus aberration, corneal astigmatism, spherical aberration, or a combination thereof. The IOL 100 can comprise an optic portion 102 and one or more haptics 104 including a first haptic 104A and a second haptic 104B coupled to and extending peripherally from the optic portion 102. The IOL 100 can be positioned within a native capsular bag in which a native lens has been removed.

In some embodiments, the haptics 104 can be coupled to and adhered to the optic portion 102. For example, the haptics 104 can be adhered to the optic portion 102 after each is formed separately. In other embodiments, the IOL 100 can be a one-piece lens such that the haptics 104 are connected to and extend from the optic portion 102. In this example embodiment, the haptics 104 are formed along with the optic portion 102 and are not adhered or otherwise coupled to the optic portion 102 in a subsequent step.

The IOL 100 can be implanted within a native capsular bag of a subject after the subject's native lens has been removed. When implanted within the native capsular bag, the optic portion 102 can be adapted to refract light that enters the eye onto the retina. When the IOL 100 is an AIOL, one or more haptics 104 can be configured to engage the capsular bag and be adapted to deform in response to ciliary muscle movement (e.g., muscle relaxation, muscle contraction, or a combination thereof) in connection with capsular bag reshaping.

Each of the haptics 104 can comprise a haptic fluid lumen 106 extending through at least part of the haptic 104. For example, the first haptic 104A can comprise a first haptic fluid lumen 106A extending through at least part of the first haptic 104A and the second haptic 104B can comprise a second haptic fluid lumen 106B extending through at least part of the second haptic 104B. The haptic fluid lumen 106 (e.g., any of the first haptic fluid lumen 106A or the second haptic fluid lumen 106B) can be in fluid communication with or fluidly 6 connected to an optic fluid chamber 108 within the optic portion 102.

The optic fluid chamber 108 can be in fluid communication with the one or more haptic fluid lumens 106 through one or more fluid channels 110. The fluid channels 110 can be conduits or passageways fluidly connecting the optic fluid chamber 108 to the haptic fluid lumens 106. The fluid channels 110 can be spaced apart from one another. For example, a pair of fluid channels 110 can be spaced apart between about 0.1 mm to about 1.0 mm. In some embodiments, each of the fluid channels 110 can have a diameter of between about 0.4 mm to about 0.6 mm.

The haptics 104 can be coupled to the optic portion 102 at a reinforced portion 112. The reinforced portion 112 can serve as a haptic-optic interface. The pair of fluid channels 110 can be defined or formed within part of the reinforced portion 112.

As shown in FIG. 1A, the optic fluid chamber 108 can be in fluid communication with the first haptic fluid lumen 106A through a first pair of fluid channels 110A. The optic fluid chamber 108 can also be in fluid communication with the second haptic fluid lumen 106B through a second pair of fluid channels 110B.

In some embodiments, the first pair of fluid channels 110A and the second pair of fluid channels 110B can be positioned substantially on opposite sides of the optic portion 102. The first pair of fluid channels 110A can be positioned substantially diametrically opposed to the second pair of fluid channels 110B. The first pair of fluid channels 110A and the second pair of fluid channels 110B can extend or be defined through part of the optic portion 102. The first pair of fluid channels 110A and the second pair of fluid channels 110B can extend or be defined through a posterior element 132 of the optic portion 102 (see, e.g., FIGS. 1B-1D).

FIG. 1A also illustrates that each of the haptics 104 (e.g., any of the first haptic 104A or the second haptic 104B) can have a proximal attachment end 114 and a distal free end 116. A haptic fluid port 152 (see, e.g., FIG. 1F) can be defined at the proximal attachment end 114 of the haptic 104. The haptic fluid port 152 can serve as an opening of the haptic fluid lumen 106. Fluid within the haptic fluid lumen 106 can flow out of the haptic fluid lumen 106 through the haptic fluid port 152 and into the optic fluid chamber 108 via the fluid channels 110 when the haptic 104 is coupled to the optic portion 102. Similarly, fluid within the optic fluid chamber can flow out of the optic fluid chamber 108 through the pair of fluid channels 110 and into the haptic fluid lumen 106 through the haptic fluid port 152.

Each of the haptics 104 can comprise a radially-outer haptic lumen wall 118 and a radially-inner haptic lumen wall 120. The radially-outer haptic lumen wall 118 (also referred to as a radially-outer lateral wall of the haptic 104) can be configured to face and contact an inner surface of a patient's capsular bag when the IOL 100 is implanted within the capsular bag. The radially-inner haptic lumen wall 120 (also referred to as a radially-inner lateral wall of the haptic 104) can be configured to face an outer peripheral surface 122 of the optic portion 102.

As previously discussed, the IOL 100 can be implanted or introduced into a patient's capsular bag after a native lens has been removed from the capsular bag. The patient's capsular bag is connected to zonule fibers which are connected to the patient's ciliary muscles. The capsular bag is elastic and ciliary muscle movements can reshape the capsular bag via the zonule fibers. For example, when the ciliary muscles relax, the zonules are stretched. This stretching pulls the capsular bag in the generally radially outward direction due to radially outward forces. This pulling of the capsular bag causes the capsular bag to elongate, creating room within the capsular bag. When the patient's native lens is present in the capsular bag, the native lens normally becomes flatter (in the anterior-to-posterior direction), which reduces the power of the lens, allowing for distance vision. In this configuration, the patient's native lens is said to be in a disaccommodated state or undergoing disaccommodation.

When the ciliary muscles contract, however, as occurs when the eye is attempting to focus on near objects, the radially inner portion of the muscles move radially inward, causing the zonules to slacken. The slack in the zonules allows the elastic capsular bag to contract and exert radially inward forces on a lens within the capsular bag. When the patient's native lens is present in the capsular bag, the native lens normally becomes more curved (e.g., the anterior part of the lens becomes more curved), which gives the lens more power, allowing the eye to focus on near objects. In this configuration, the patient's native lens is said to be in an accommodated state or undergoing accommodation.

In embodiments where the IOL 100 is an AIOL, the radially-outer haptic lumen wall 118 of the implanted AIOL can directly engage with or be in physical contact with the portion of the capsular bag that is connected to the zonules or zonule fibers. Therefore, the radially-outer haptic lumen wall 118 of the AIOL can be configured to respond to capsular bag reshaping forces that are applied radially when the zonules relax and stretch as a result of ciliary muscle movements.

For example, when the ciliary muscles contract, the peripheral region of the elastic capsular bag reshapes and applies radially inward forces on the radially-outer haptic lumen wall 118 of each of the haptics 104. When the IOL 100 is an AIOL, the radially-outer haptic lumen wall 118 can deform or otherwise change shape and this deformation or shape-change can cause the volume of the haptic fluid lumen 106 to decrease. When the volume of the haptic fluid lumen 106 decreases, the fluid within the haptic fluid lumen 106 is moved or pushed into the optic fluid chamber 108. The optic portion 102 of the AIOL can change shape in response to fluid entering the optic fluid chamber 108 from the haptic fluid lumen 106. This can increase the base power or base spherical power of the AIOL and allow a patient with the AIOL implanted within the eye of the patient to focus on near objects. In this state, the adjustable AIOL can be considered to have undergone accommodation.

When the ciliary muscles relax, the peripheral region of the elastic capsular bag is stretched radially outward and the capsular bag elongates and more room is created within the capsular bag. The radially-outer haptic lumen wall 118 of the haptics 104 can be configured to respond to this capsular bag reshaping by returning to its non-deformed or non-stressed configuration. This causes the volume of the haptic fluid lumen 106 to increase or return to its non-deformed volume. This increase in the volume of the haptic fluid lumen 106 can cause the fluid within the optic fluid chamber 108 to be drawn out or otherwise flow out of the optic fluid chamber 108 and back into the haptic fluid lumen 106. Fluid moves out of the optic fluid chamber 108 into the haptic fluid lumen 106 through the same fluid channels 110 formed within the optic portion 102.

The optic portion 102 of the AIOL can change shape in response to fluid exiting the optic fluid chamber 108 and into the haptic fluid lumen 106. This can decrease the base power or base spherical power of the AIOL and allow a patient with the AIOL implanted within the eye of the patient to focus on distant objects or provide for distance vision. In this state, the AIOL can be considered to have undergone disaccommodation.

When the IOL 100 is an AIOL, the radially-outer haptic lumen walls 118 of the haptics 104 can be made thinner than the radially-inner haptic lumen walls 120 to allow the haptics 104 to maintain a high degree of sensitivity to radial forces applied to an equatorial region of the haptics 104 by capsular bag reshaping as a result of ciliary muscle movements. As shown in FIGS. 1B to 1E, the radially-inner haptic lumen walls 120 of the haptics 104 can be designed to be thicker or bulkier than the radially-outer haptic lumen walls 118 to provide the haptics with stiffness or resiliency in the anterior-to-posterior direction. In certain embodiments, the radially-inner haptic lumen wall 120 can taper in shape as the radially-inner haptic lumen wall 120 gets closer to the optic portion 102. When designed in this manner, the haptics 104 can be less sensitive to capsular bag forces applied in the anterior-to-posterior direction. For example, when capsular bag forces are applied to the haptics 104 in the anterior-to-posterior direction, less fluid movement occurs between the haptic fluid lumens 106 and the optic fluid chamber 108 than when forces are applied in the radial direction. Since less fluid movement occurs, less changes in the base power of the AIOL occur.

Although FIGS. 1A to 1F illustrate the IOL 100 as an AIOL, it is contemplated by this disclosure that the IOL 100 can also be a non-accommodating or static-focus adjustable IOL 19 and that an external energy (e.g., laser light) can be directed at part(s) of the non-accommodating or static-focus adjustable IOL to adjust the base power of the non-accommodating or static-focus adjustable IOL. Examples of non-accommodating or static-focus adjustable IOLs are discussed in U.S. Pat. Pub. No. 2021/0100649, the content of which is incorporated herein by reference in its entirety.

In some embodiments, the IOL 100 can be designed such that a gap 124 or void space radially separates the radially-inner haptic lumen wall 120 of the haptic 104 from the outer peripheral surface 122 of the optic portion 102. This can allow portions of the haptic 104 to change shape or expand in response to an external energy such as a laser light 125 (see, e.g., FIGS. 1D and 1E) directed at the haptic 104.

Figure 1B:
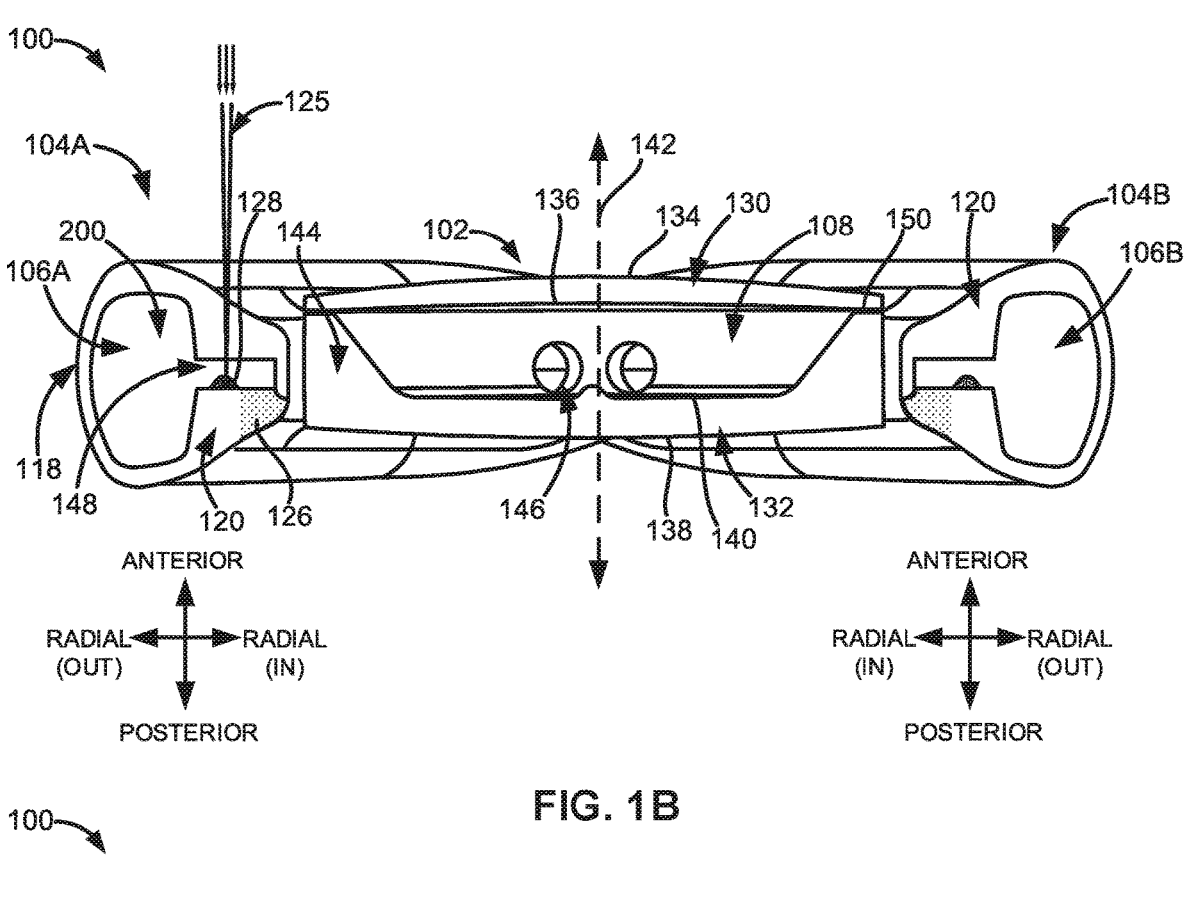
FIGS. 1B and 1C illustrate cross-sectional views of the IOL of FIG. 1A taken along cross-section A-A and a first composite material within the IOL decreasing in size in response to an external energy applied to the first composite material.
Figure 1C:
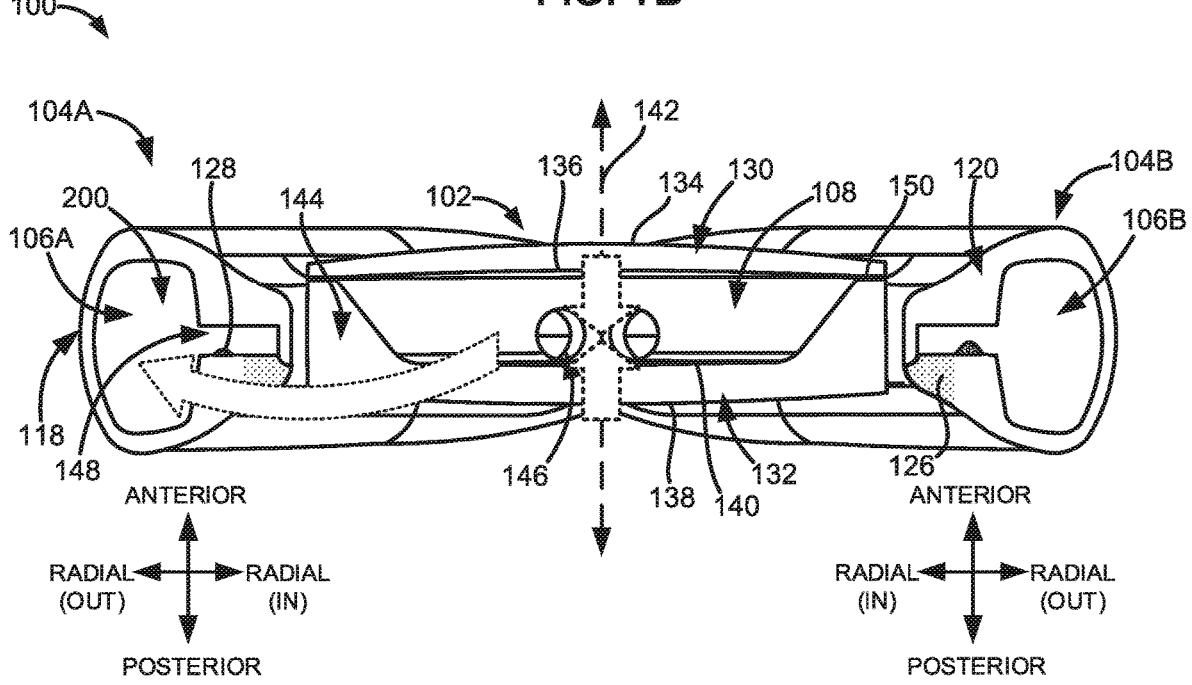
Figures 1D, 1E:
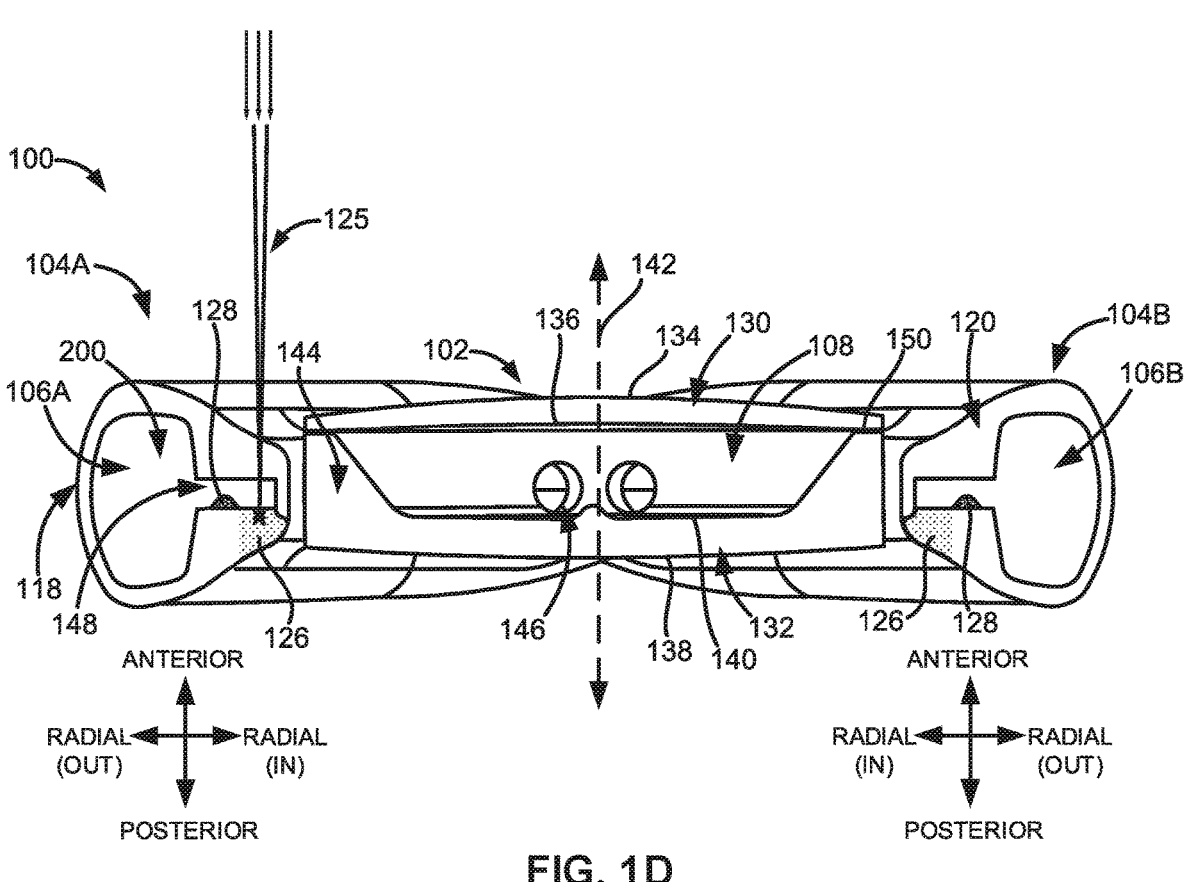
FIGS. 1D and 1E illustrate cross-sectional views of the IOL of FIG. 1A taken along cross-section A-A and one portion of a second composite material increasing in size in response to an external energy applied to the second composite material.
Figure 2A:
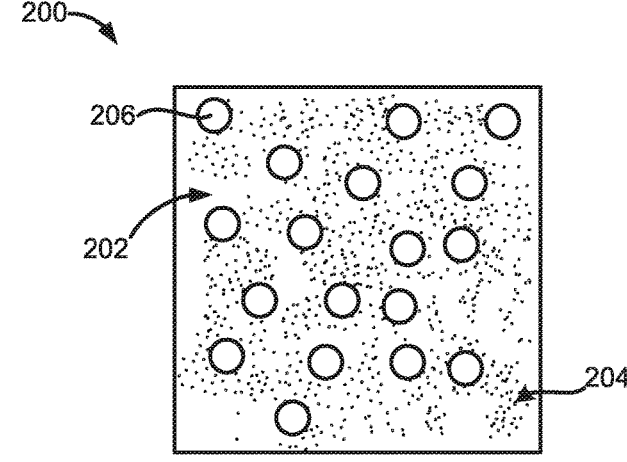
FIG. 2A is a pictorial representation of a first composite material.
Figure 2B:
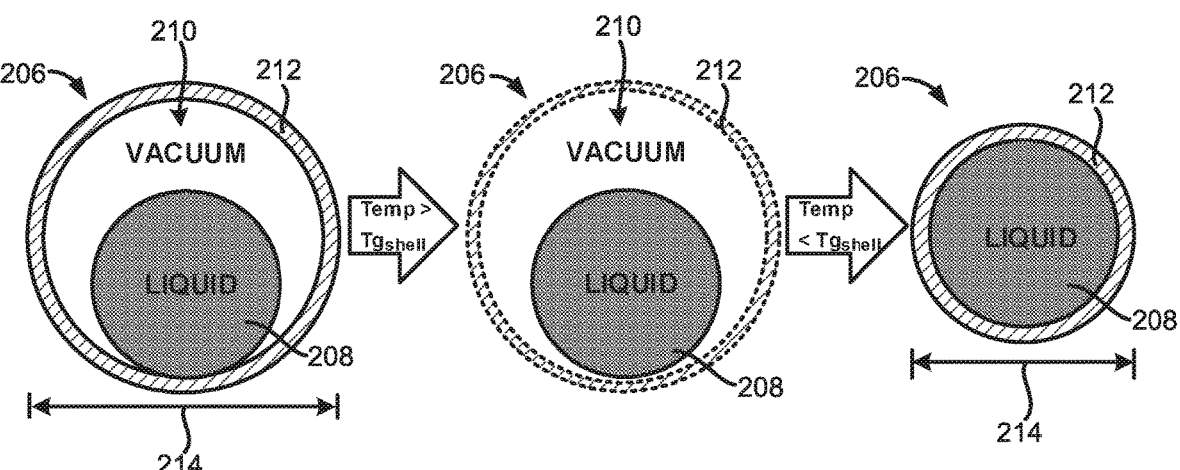
FIG. 2B is a pictorial representation of a shrinkable and/or burstable microsphere of the first composite material.
Figure 2C:
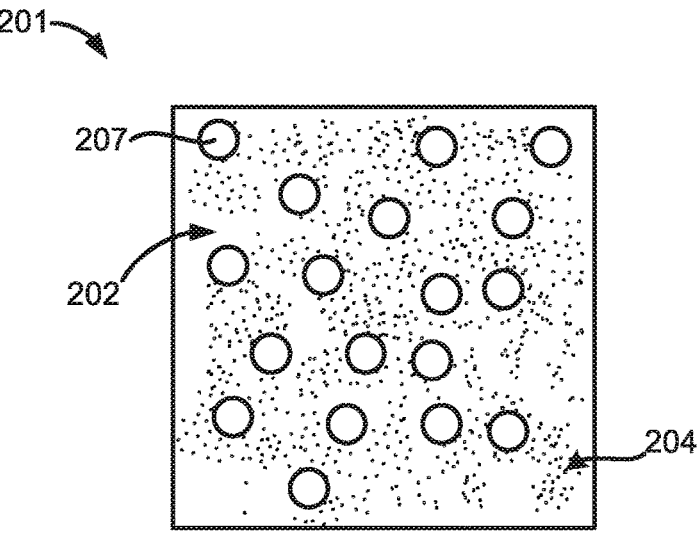
FIG. 2C is a pictorial representation of a second composite material used to make at least part of a haptic of the IOL.

FIG. 1A also illustrates that at least one of the haptics 104 can comprise a shrinkable component 128 made of a first composite material 200 (see, e.g., FIG. 2A) and a lumen filler 126 made of a second composite material 201 (see, e.g., FIG. 2C). As will be discussed in more detail in later sections, the first composite material 200 can comprise or be made in part of an energy absorbing constituent, a plurality of shrinkable and/or burstable microspheres, and a cross-linked copolymer used to make the rest of the haptic 104. The shrinkable component 128 made of the first composite material 200 can be configured to shrink or decrease in size in response to the laser light 125 (see, e.g., FIGS. 1B and 1C) directed at the first composite material 200. The second composite material 201 can comprise or be made in part of an energy absorbing constituent, a plurality of expandable microspheres, and a cross-linked copolymer used to make the rest of the haptic 104. At least part of the lumen filler 126 made of the second composite material 201 can be configured to expand or increase in size in response to the laser light 125 (see, e.g., FIGS. 1D and 1E) directed at the lumen filler 126.

When the laser light 125 is applied to the shrinkable component 128 made of the first composite material 200, the shrinkable component 128 can shrink or decrease in size and the shrinkage or contraction of the shrinkable component 128 can increase a volume of the haptic fluid lumen 106 and cause fluid within the optic fluid chamber 108 to be drawn into the haptic fluid lumen 106. This can also cause the optic portion 102 to change shape (e.g., cause the 16 anterior or posterior elements of the optic portion 102 to become less curved or flatter) leading to a decrease in the base power of the optic portion 102.

Alternatively, when laser light 125 is applied to the lumen filler 126 made of the second composite material 201, the lumen filler 126 can expand and the expansion of the lumen filler 126 can decrease the volume of the haptic fluid lumen 106 and cause fluid within the haptic fluid lumen 106 to be displaced into the optic fluid chamber 108. This can cause the optic portion 102 to change shape (e.g., cause the anterior or posterior elements of the optic portion 102 to become more curved) leading to an increase in the base power of the optic portion 102.

FIGS. 1B and 1C illustrate cross-sectional views of the IOL 100 of FIG. 1A taken along cross-section A-A. As shown in FIGS. 1B and 1C, the optic portion 102 can comprise an anterior element 130 and a posterior element 132. The fluid-filled optic fluid chamber 108 can be defined in between the anterior element 130 and the posterior element 132.

The anterior element 130 can comprise an anterior optical surface 134 and an anterior inner surface 136 opposite the anterior optical surface 134. The posterior element 132 can comprise a posterior optical surface 138 and a posterior inner surface 140 opposite the posterior optical surface 138. Any of the anterior optical surface 134, the posterior optical surface 138, or a combination thereof can be considered and referred to as an external optical surface. The anterior inner surface 136 and the posterior inner surface 140 can face the optic fluid chamber 108. At least part of the anterior inner surface 136 and at least part of the posterior inner surface 140 can serve as chamber walls of the optic fluid chamber 108.

As shown in FIGS. 1B and 1C, the optic portion 102 can have an optical axis 142 extending in an anterior-to-posterior direction through a center of the optic portion 102. The optical axis 142 can extend through the centers of both the anterior element 130 and the posterior element 132.

The thickness of the anterior element 130 can be greater at or near the optical axis 142 than at the periphery of the anterior element 130. In some embodiments, the thickness of the anterior element 130 can increase gradually from the periphery of the anterior element 130 toward the optical axis 142.

In certain embodiments, the thickness of the anterior element 130 at or near the optical axis 142 can be between about 0.45 mm and about 0.55 mm. In these and other embodiments, the thickness of the anterior element 130 near the periphery can be between about 0.20 mm and about 0.40 mm. Moreover, the anterior inner surface 136 of the anterior element 130 can have less curvature or be flatter than the anterior optical surface 134.

The thickness of the posterior element 132 can be greater at or near the optical axis 142 than portions of the posterior element 132 radially outward from the optical axis 142 but prior to reaching a raised periphery 144 of the posterior element 132. The thickness of the posterior element 132 can gradually decrease from the optical axis 142 to portions radially outward from the optical axis 142 (but prior to reaching the raised periphery 144). As shown in FIGS. 1B and 1C, the thickness of the posterior element 132 can increase once again from a radially inner portion of the raised periphery 144 to a radially outer portion of the raised periphery 144.

In certain embodiments, the thickness of the posterior element 132 at or near the optical axis 142 can be between about 0.45 mm and about 0.55 mm. In these and other embodiments, the thickness of the posterior element 132 radially outward from the optical axis (but prior to reaching the raised periphery 144) can be between about 0.20 mm and about 0.40 mm. The thickness of the posterior element 132 near the radially outer portion of the raised periphery 144 can be between about 1.00 mm and 1.15 mm. Moreover, the posterior inner surface 140 of the posterior element 132 can have less curvature or be flatter than the posterior optical surface 138.

The optic portion 102 can have a base power or base spherical power. The base power of the optic portion 102 can be configured to change based on an internal fluid pressure within the fluid-filled optic fluid chamber 108. The base power of the optic portion 102 can be configured to increase or decrease as fluid enters or exits the fluid-filled optic fluid chamber 108.

As shown in FIGS. 1B and 1C, each of the haptics 104 can comprise a shrinkable component 128 made of a first composite material 200 (see, e.g., FIG. 2A). The first composite material 200 can be configured to respond to an external energy, such as laser light 125, applied to the first composite material 200.

In some embodiments, the shrinkable component 128 can be adhered or otherwise coupled to a part of the radially-inner haptic lumen wall 120 of each of the haptics 104. As shown in FIGS. 1B and 1C, the shrinkable component 128 can be adhered or otherwise coupled to a part of a posterior portion of the radially-inner haptic lumen wall 120. In other embodiments not shown in the figures, the shrinkable component 128 can be adhered or otherwise coupled to a part of an anterior portion of the radially-inner haptic lumen wall 120.

The shrinkable component 128 can be located partly within the channel 148 formed along the radially-inner haptic lumen wall 120 of each of the haptics 104. The shrinkable component 128 can take up space within the channel 148 prior to being exposed to the external energy.

In other embodiments, at least part of the radially-inner haptic lumen wall 120 can be made of the first composite material 200. For example, at least part of the posterior or anterior portion of the radially-inner haptic lumen wall 120 can be made of the first composite material 200.

In response to the external energy directed at the shrinkable component 128, the shrinkable component 128 can shrink or decrease in size. Since the shrinkable component 128 formerly takes up space within the channel 148, reducing the size of the shrinkable component can increase the space available within the channel 148. Moreover, since the channel 148 is in fluid communication with the haptic fluid lumen 106, when the shrinkable component 128 decreases in size, the volume of the haptic fluid lumen 106 can increase. This can allow fluid within the optic fluid chamber 108 to be drawn into the haptic fluid lumen 106. As a result, at least one of the anterior element 130 and the posterior element 132 can decrease its curvature and the base power of the optic portion 102 can decrease in response to the laser light 125 directed at the shrinkable component 128 made of the first composite material 200.

As shown in FIGS. 1B and 1C, the shrinkable component 128 can initially be a mass extending into the channel 148. The volume of the mass can decrease in response to the external energy directed at the shrinkable component 128. When the volume of the mass decreases, the volume of available space within the channel 148 and the volume of the haptic fluid lumen 106 can increase, thereby drawing fluid out of the optic fluid chamber 108 and into the haptic fluid lumen 106.

The base power of the optic portion 102 can be configured to decrease as fluid exits or is drawn out of the fluid-filled optic fluid chamber 108 into the haptic fluid lumen(s) 106, as depicted in FIG. 1C. For example, the anterior element 130 of the optic portion 102 can be configured to decrease its curvature (or flatten out) in response to the fluid exiting the optic fluid chamber 108. Also, for example, the posterior element 132 of the optic portion 102 can be configured to decrease its curvature (or flatten out) in response to the fluid exiting the optic fluid chamber 108. In further embodiments, both the anterior element 130 and the posterior element 132 can be configured to decrease their curvatures in response to the fluid exiting the optic fluid chamber 108.

It should be noted that although FIG. 1C illustrates the fluid exiting the optic fluid chamber 108 to the haptic fluid lumen 106 using the curved broken-line arrow, fluid exits the optic fluid chamber 108 via the fluid channels 110 and apertures 146 defined along the posterior element 132. The apertures 146 can be holes or openings defined along the posterior element 132 that serve as terminal ends of the fluid channels 110. When the IOL 100 comprises a pair of fluid channels 110, the pair of apertures 146 serving as ends of the fluid channels 110 can be spaced apart from one another between about 0.1 mm to about 1.0 mm.

One technical problem faced by the applicants is that once an IOL 100 is implanted within a capsular bag of a patient, an aggressive healing response by tissue within the capsular bag can squeeze or contract portions of the IOL 100 and drive the optical power higher than initially anticipated. Another technical problem faced by the applicants is that the pre-operative biometry measurements made on a patient's eye may be incorrect, leading to lenses with the wrong lens power being prescribed and implanted within the patient. Moreover, yet another technical problem faced by the applicants is that a patient's cornea or muscles within the eye may change as a result of injury, disease, or aging. In such cases, it may also be necessary to adjust the patient's implanted IOLs to account for such changes. One technical solution discovered and developed by the applicants is to design an IOL 100 that can be adjusted post-operatively (i.e., post-implantation) such that the optical power of the IOL 100 can be decreased or reduced to account for such changes or errors. Such a solution should also not overly complicate the design of such lenses and still allow the lenses to be cost-effectively manufactured.

In some embodiments, the fluid within the optic fluid chamber 108 and the haptic fluid lumen(s) 106 can be an oil. More specifically, in certain embodiments, the fluid within the optic fluid chamber 108 and the haptic fluid lumen(s) 106 can be a silicone oil or fluid. For example, the fluid can be a silicone oil made in part of a diphenyl siloxane. In other embodiments, the fluid can be a silicone oil made in part of a ratio of two dimethyl siloxane units to one diphenyl siloxane unit. More specifically, in some embodiments, the fluid can be a silicone oil made in part of diphenyltetramethyl cyclotrisiloxane or a copolymer of diphenyl siloxane and dimethyl siloxane. In further embodiments, the fluid can be a silicone oil comprising branched polymers.

The fluid (e.g., the silicone oil) can be index matched with a lens body material used to make the optic portion 102. When the fluid is index matched with the lens body material, the entire optic portion 102 containing the fluid can act as a single lens. For example, the fluid can be selected so that it has a refractive index of between about 1.48 and 1.53 (or between about 1.50 and 1.53). In some embodiments, the fluid (e.g., the silicone oil) can have a polydispersity index of between about 1.2 and 1.3. In other embodiments, the fluid (e.g., the silicone oil) can have a polydispersity index of between about 1.3 and 1.5. In other embodiments, the fluid (e.g., the silicone oil) can have a polydispersity index of between about 1.1 and 1.2. Other example fluids are described in U.S. Patent Publication No. 2018/0153682, which is herein incorporated by reference in its entirety.

The optic portion 102 can be made in part of a deformable or flexible material. In some embodiments, the optic portion 102 can be made in part of a deformable or flexible polymeric material. For example, the anterior element 130, the posterior element 132, or a combination thereof can be made in part of a deformable or flexible polymeric material. The one or more haptics 104 (e.g., the first haptic 104A, the second haptic 104B, or a combination thereof) can be made in part of the same deformable or flexible material as the optic portion 102. In other embodiments, the one or more haptics 104 can be made in part of different materials from the optic portion 102.

In some embodiments, the optic portion 102 can comprise or be made in part of a lens body material. The lens body material can be made in part of a cross-linked copolymer comprising a copolymer blend. The copolymer blend can comprise an alkyl acrylate or methacrylate, a fluoro-alkyl (meth)acrylate, and a phenyl-alkyl acrylate. It is contemplated by this disclosure and it should be understood by one of ordinary skill in the art that these types of acrylic cross-linked copolymers can be generally copolymers of a plurality of acrylates, methacrylates, or a combination thereof and the term "acrylate" as used herein can be understood to mean acrylates, methacrylates, or a combination thereof interchangeably unless otherwise specified. The cross-linked copolymer used to make the lens body material can comprise an alkyl acrylate in the amount of about 3% to 20% (wt %), a fluoro-alkyl acrylate in the amount of about 10% to 35% (wt %), and a phenyl-alkyl acrylate in the amount of about 50% to 80% (wt %). In some embodiments, the cross-linked copolymer can comprise or be made in part of an n-butyl acrylate as the alkyl acrylate, trifluoroethyl methacrylate as the fluoro-alkyl acrylate, and phenylethyl acrylate as the phenyl-alkyl acrylate. More specifically, the cross-linked copolymer used to make the lens body material can comprise n-butyl acrylate in the amount of about 3% to 20% (wt %) (e.g., between about 12% to 16%), trifluoroethyl methacrylate in the amount of about 10% to 35% (wt %) (e.g., between about 17% to 21%), and phenylethyl acrylate in the amount of about 50% to 80% (wt %) (e.g., between about 64% to 67%).

The final composition of the cross-linked copolymer used to make the lens body material can also comprise a cross-linker or cross-linking agent such as ethylene glycol dimethacrylate (EGDMA). For example, the final composition of the cross-linked copolymer used to make the lens body material can also comprise a cross-linker or cross-linking agent (e.g., EGDMA) in the amount of about 1.0%. The final composition of the cross-linked copolymer used to make the lens body material can also comprise an initiator or initiating agent (e.g., Perkadox 16) and a UV absorber.

The one or more haptics 104 can comprise or be made in part of a haptic material. The haptic material can comprise or be made in part of a cross-linked copolymer comprising a copolymer blend. The copolymer blend can comprise an alkyl acrylate, a fluoro-alkyl acrylate, and a phenyl-alkyl acrylate. For example, the cross-linked copolymer used to make the haptic material can comprise an alkyl acrylate in the amount of about 10% to 25% (wt %), a fluoro-alkyl acrylate in the amount of about 10% to 35% (wt %), and a phenyl-alkyl acrylate in the amount of about 50% to 80% (wt %). In some embodiments, the cross-linked copolymer used to make the haptic material can comprise n-butyl acrylate in the amount of about 10% to 25% (wt %) (e.g., between about 19% to about 23%), trifluoroethyl methacrylate in the amount of about 10% to 35% (wt %) (e.g., between about 14% to about 18%), and phenylethyl acrylate in the amount of about 50% to 80% (wt %) (e.g., between about 58% to about 62%). The final composition of the cross-linked copolymer used to make the haptic material can also comprise a cross-linker or cross-linking agent, such as EGDMA, in the amount of about 1.0%. The final composition of the cross-linked copolymer used to make the haptic material can also comprise a number of photoinitiators or photoinitiating agents (e.g., camphorquinone, 1-phenyl-1,2-propanedione, and 2-ethylhexyl-4-(dimenthylamino)benzoate).

In some embodiments, the refractive index of the lens body material can be between about 1.48 and about 1.53. In certain embodiments, the refractive index of the lens body material can be between about 1.50 and about 1.53 (e.g., about 1.5178).

The anterior element 130 can be attached or otherwise adhered to the posterior element 132 via adhesives 150 or an adhesive layer. The adhesive layer can be substantially annular-shaped. The adhesives 150 or adhesive layer can be positioned at a peripheral edge of the optic portion 102 in between the anterior element 130 and the posterior element 132. For example, the adhesives 150 can be positioned on top of the raised periphery 144 of the posterior element 132.

The adhesives 150 or adhesive layer can comprise or be made in part of a biocompatible adhesive. The adhesives 150 or adhesive layer can comprise or be made in part of a biocompatible polymeric adhesive.

The adhesives 150 or adhesive layer can comprise or be made in part of a cross-linkable polymer precursor formulation. The cross-linkable polymer precursor formulation can comprise or be made in part of a copolymer blend, a hydroxyl-functional acrylic monomer, and a photoinitiator.

The copolymer blend can comprise an alkyl acrylate (e.g., n-butyl acrylate in the amount of about 41% to about 45% (wt %)), a fluoro-alkyl acrylate (e.g., trifluoroethyl methacrylate in the amount of about 20% to about 24% (wt %)), and a phenyl-alkyl acrylate (phenylethyl acrylate in the amount of about 28% to about 32% (wt %)). The hydroxyl-functional acrylic monomer can be 2-hydroxyethyl acrylate (HEA). The photoinitiator can be used to facilitate curing of the adhesive. For example, the photoinitiator can be Darocur 4265 (a 50/50 blend of diphenyl(2,4,6-trimethylbenzoyl) phosphine oxide and 2-hydroxy2-methylpropiophenone).

In some embodiments, the same adhesives 150 used to bond the anterior element 130 to the posterior element 132 can also be used to bond or affix the one or more haptics 104 to the optic portion 102.

FIGS. 1D and 1E illustrate that one or more portions of the IOL 100 can be made of a second composite material 201 (see, e.g., FIG. 2C) configured to respond to an external energy, such as laser light 125, applied to the second composite material 201. The second composite material 201 can be positioned or integrated within each of the haptics 104 in such a way that the second composite material 201 acts as a lumen filler 126. For example, laser light 125 can be directed or otherwise applied to the lumen filler 126 to cause at least part of the lumen filler to expand and grow in size. This expansion can manifest itself as a part of the lumen filler 126 expanding or growing into the channel 148 (see, for example, FIG. 1E). More specifically, this expansion can manifest itself as an anterior portion of the lumen filler 126 growing or rising into the channel 148.

Since the channel 148 is in fluid communication with or otherwise exposed to the haptic fluid lumen 106, the growth or expansion of the lumen filler 126 into the channel 148 can decrease a volume of the haptic fluid lumen 106. This can cause fluid within the haptic fluid lumen 106 to be pushed or otherwise displaced into the optic fluid chamber 108. As a result, at least one of the anterior element 130 and the posterior element 132 can increase its curvature and the base power of the optic portion 102 can increase in response to the laser light 125 directed at the lumen filler 126.

The base power of the optic portion 102 can be configured to increase as fluid enters the fluid-filled optic fluid chamber 108 from the haptic fluid lumen 106, as depicted in FIG. 1E using the curved broken-line arrows. For example, the anterior element 130 of the optic portion 102 can be configured to increase its curvature in response to the fluid entering the optic fluid chamber 108. Also, for example, posterior element 132 of the optic portion 102 can be configured to increase its curvature in response to the fluid entering the optic fluid chamber 108. In further embodiments, both the anterior element 130 and the posterior element can be configured to increase their curvatures in response to the fluid entering the optic fluid chamber 108.

In some embodiments, the lumen filler 126 can be positioned posterior to the channel 148. In these embodiments, the lumen filler 126 can replace or act as part of the posterior portion of the radially-inner haptic lumen wall 120. The lumen filler 126 can also be positioned radially inward of the portion of the haptic fluid lumen 106 that is not the channel 148.

At least part of the lumen filler 126 can be in fluid communication with the channel 148. For example, at least part of an anterior portion or layer of the lumen filler 126 can be in fluid communication with or otherwise exposed to the channel 148.

As shown in FIGS. 1D and 1E, in some embodiments, a radially outer lateral side of the lumen filler 126 is not in fluid communication with the haptic fluid lumen 106. In these embodiments, the radially outer lateral side of the lumen filler 126 is separated from the haptic fluid lumen 106 by a part of the haptic 104 not made of the composite material 200.

It should be noted that although FIGS. 1D and 1E illustrate the fluid entering the optic fluid chamber 108 from the haptic fluid lumens 106 using the curved broken-line arrows, fluid enters the optic fluid chamber 108 via the fluid channels 110 and apertures 146 defined along the posterior element 132.

FIGS. 1A to 1E also illustrate that the IOL 100 can comprise one or more shrinkable components 128, lumen fillers 126, or a combination thereof. For example, each of the haptics of the IOL 100 can comprise both a shrinkable component 128 and a lumen filler 126.

Moreover, FIGS. 1A to 1E illustrate that, in some embodiments, the shrinkable component 128 can be positioned radially outward of the lumen filler 126. In these embodiments, the lumen filler 126 can be positioned radially inward of the shrinkable component 128 or radially closer to the optic portion 102.

In other embodiments not shown in the figures but contemplated by this disclosure, the lumen filler 126 can be positioned radially outward of the shrinkable component 128 and the shrinkable component 128 can be positioned radially closer to the optic portion 102.

The shrinkable component 128 can be coupled directly to a portion of the haptic 104 not made of the second composite material 201. More specifically, the section of the haptic directly anterior or posterior to the shrinkable component 128 is not made of the second composite material 201.

For example, as shown in FIGS. 1B-1E, the shrinkable component 128 can be coupled directly to and positioned anterior to a posterior portion of the radially-inner haptic lumen wall 120 that is not made of the second composite material 201. In this example, the shrinkable component 128 can protrude or otherwise extend into the channel 148.

In other embodiments not shown in the figures but contemplated by this disclosure, the shrinkable component 128 can be coupled directly to a radially outward facing side of the posterior portion of the radially-inner haptic lumen wall 120. In these embodiments, the shrinkable component 128 can protrude or otherwise extend directly into the haptic fluid lumen 106.

In further embodiments not shown in the figures but contemplated by this disclosure, at least part of the radially-inner haptic lumen wall 120 positioned radially outward of the lumen filler 126 can be made of the first composite material 200 such that this part of the radially-inner haptic lumen wall 120 acts as the shrinkable component 128.

In all such embodiments, the shrinkable component 128 is configured to shrink or reduce in size in response to an external energy (e.g., laser light 125) directed at the shrinkable component 128. This reduction in size of the shrinkable component 128 can free up space within the haptic fluid lumen 106 and allow fluid within the fluid-filled optic fluid chamber 108 to be drawn into the haptic fluid lumen 106. This can, in turn, decrease the optic power of the optic portion 102.

Figure 1F:
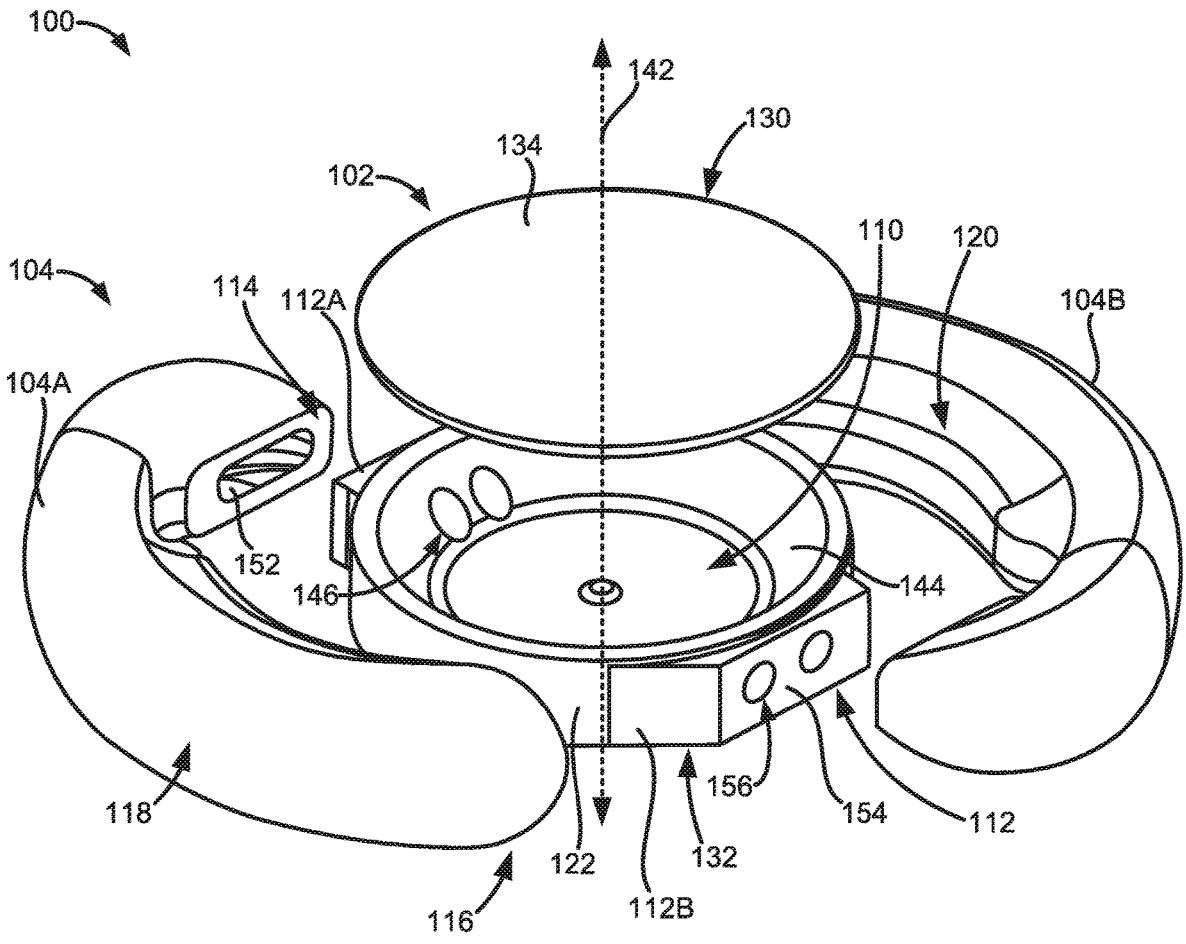
FIG. 1F illustrates an exploded view of the IOL of FIG. 1A.

FIG. 1F also illustrates that each of the haptics 104 (e.g., any of the first haptic 104A or the second haptic 104B) can have a proximal attachment end 114 and a closed distal free end 116. A haptic fluid port 152 can be defined at the proximal attachment end 114 of the haptic 104. The haptic fluid port 152 can serve as a chamber opening of the haptic fluid lumen 106. Fluid within the haptic fluid lumen 106 can flow out of the haptic fluid lumen 106 through the haptic fluid port 152 and into the optic fluid chamber 108 via the pair of fluid channels 110 when the haptic 104 is coupled to the optic portion 102. Similarly, fluid within the optic fluid chamber 108 can flow out of the optic fluid chamber 108 through the pair of fluid channels 110 and into the haptic fluid lumen 106 through the haptic fluid port 152. A pair of outer apertures 156 and inner apertures 146 can serve as ends of the fluid channels 110.

As shown in FIGS. 1A and 1F, each of the haptics 104 can be coupled to the optic portion 102 at a reinforced portion 112. For example, the first haptic 104A can be coupled or be attached to the optic portion 102 at a first reinforced portion 112A and the second haptic 104B can be coupled or be attached to the optic portion 102 at the second reinforced portion 112B.

More specifically, the proximal attachment end 114 can be coupled to the protruding outer surface 154 of the posterior element 132. The protruding outer surface 154 can also be referred to as a "landing" or "haptic attachment landing." The protruding outer surface 154 can extend out radially from an outer peripheral surface 122 of the optic portion 102. For example, the protruding outer surface 154 can extend out radially from an outer peripheral surface 122 of the posterior element 132 of the optic portion 102. The protruding outer surface 154 can extend out radially from the outer peripheral surface 122 between about 10 microns and 1.0 mm or between about 10 microns and 500 microns.

The proximal attachment end 114 can have a substantially flat surface to adhere or otherwise couple to a substantially flat surface of the protruding outer surface 154. When the proximal attachment end 114 is coupled to the protruding outer surface 154, the haptic fluid port 152 can surround the outer apertures 156 of the fluid channels 110. The haptics 104 can be coupled or adhered to the optic portion 102 via biocompatible adhesives 150. In some embodiments, the adhesives 150 can be the same adhesives used to couple or adhere the anterior element 130 to the posterior element 132.

FIG. 2A is a graphic representation of one embodiment of a first composite material 200 comprising a composite base material 202, an energy absorbing constituent 204, and a plurality of shrinkable and/or burstable microspheres 206. As previously discussed, the shrinkable component(s) 128 can be made of the first composite material 200. In some embodiments, the shrinkable component(s) 128 can be adhered or otherwise coupled to a part of the haptic 104 such as the radially-inner haptic lumen wall 120. In other embodiments, at least part of the haptic 104 (e.g., part of the radially-inner haptic lumen wall 120) can be made of the first composite material 200.

The composite base material 202 can be comprised of hydrophobic acrylic materials. For example, the composite base material 202 can be comprised of phenylethyl acrylate (PEA), a phenylethyl methacrylate (PEMA), or a combination thereof.

In one example embodiment, the composite base material 202 can comprise a methacrylate-functional or methacrylicpolymer (as discussed above) in the amount of about 50% to about 65% (e.g., about 55% to about 60%) (wt %), the reactive acrylic monomer diluent lauryl methacrylate (SR313) in the amount of about 32% to about 38% (e.g., about 32.70%) (wt %), the reactive acrylic monomer diluent adamantly methacrylate (ADMA) in the amount of about 5% to about 9% (e.g., about 7.30%) (wt %).

Table 1 below provides an example formulation for the first composite material 200:

TABLE 1

| FORMULATION OF FIRST COMPOSITE MATERIAL (WT % ) | |
| --- | --- |
| Cross-linkable polymer (in two steps from precursor formulation, as described above) | 1.47% 2-hydroxyethyl acrylate (HEA)<br>1.96% Darocur 4265 (photoinitiator)<br>43.49% n-butylacrylate (nBA)<br>30.21% 2-phenylethylacrylate (PEA)<br>22.87% 2,2,2-trifluoroethylmethacrylate (TFEMA) |
| Composite base material | 60.00% cross-linkable polymer<br>32.70% lauryl methacrylate (SR313)<br>7.30% 1-adamantyl methacrylate (ADMA) |
| Composite base material with red energy absorbing colorant | 99.50% composite base material<br>0.50% Disperse Red 1 dye |
| Composite base material with black energy absorbing colorant | 99.95% composite base material<br>0.05% graphitized mesoporous carbon black |
| Final formulation of first composite material | 92.70% to 72.70% composite base material with red or black energy absorbing colorant<br>5.00% to 25.00% shrinkable and/or burstable micro-spheres<br>1.00% Luperox peroxide (thermal initiator)<br>1.30% Omnirad 2022 | functional cross-linkable polymer and reactive acrylic monomer diluents including lauryl methacrylate (n-dodecyl methacrylate or SR313) and 1-adamantyl methacrylate (ADMA). By controlling the amount of lauryl methacrylate (SR313) to ADMA, the overall corresponding hardness (i.e., more ADMA) or softness (i.e., more SR313) of the cured first composite material 200 can be controlled. The methacrylate-functional or methacrylic-functional cross-linkable polymer can be made using the cross-linkable polymer precursor formulation.

In other embodiments, the monomer diluent can be or comprise phenylethyl acrylate (PEA). In these embodiments, PEA can be used as the monomer diluent instead of SR313.

The cross-linkable polymer precursor formulation can comprise the same copolymer blend used to make the optic portion 102 and the haptics 104.

The copolymer blend can comprise an alkyl acrylate or methacrylate (e.g., n-butyl acrylate), a fluoro-alkyl (meth) acrylate (e.g., trifluoroethyl methacrylate), and a phenyl-alkyl acrylate (e.g., phenylethyl acrylate). For example, the copolymer blend can comprise n-butyl acrylate in the amount of about 41% to about 45% (wt %), trifluoroethyl methacrylate in the amount of about 20% to about 24% (wt %), and phenylethyl acrylate in the amount of about 28% to about 32% (wt %). The cross-linkable polymer precursor formulation can comprise or be made in part of the copolymer blend, a hydroxyl-functional acrylic monomer (e.g., HEA), and a photoinitiator (e.g., Darocur 4265 or a 50/50 blend of diphenyl(2,4,6-trimethylbenzoyl)-phosphine oxide and 2-hydroxy2-methylpropiophenone).

The composite base material 202 can comprise the methacrylate-functional or methacrylic-functional cross-linkable In some embodiments, the first composite material 200 can be made in several operations. The first operation can comprise preparing an uncolored composite base material 202. The second operation can comprise mixing the composite base material 202 with the energy absorbing constituent 204, the shrinkable and/or burstable microspheres 206, and initiators such as one or more photoinitiators, thermal initiators, or a combination thereof. The third operation can comprise placing the uncured first composite material 200 into a desired location within the haptics 104 (e.g., in proximity to the channel 148), and curing the first composite material 200 in place.

The uncolored composite base material 202 can be mixed with the energy absorbing constituent 204 such as a dye (e.g., Disperse Red 1 dye) or pigment (graphitized carbon black). The energy absorbing constituent 204 will be discussed in more detail below.

In some embodiments, the shrinkable and/or burstable microspheres 206 can make up about 5.0% to about 25.0% by weight of a final formulation of the first composite material 200 (see Table 1) of the first composite material 200.

The photoinitiator can be Omnirad 2022 (bis(2,4,6-trimethylbenzoyl)phenyl-phosphineoxide/2-hydroxy-2-methyl-1-phenyl-propan-1-one). The photoinitiator can make up about 1.30% by weight of a final formulation of the first composite material 200 (see, e.g., Table 1). In addition, the first composite material 200 can also comprise a thermal initiator. The thermal initiator can make up about 1.00% by weight of a final formulation of the composite material 200 (see, e.g., Table 1). In some embodiments, the thermal initiator can be a dialkyl peroxide such as Luperox® peroxide. In other embodiments, the thermal initiator can be Perkadox.

In some embodiments, the energy absorbing constituent 204 can absorb the external energy (e.g., laser energy) and convert the energy to heat. The heat energy can be conducted to the shrinkable and/or burstable microspheres 206 (e.g., via the composite base material 202) to shrink the shrinkable microspheres or burst the burstable microspheres.

Although FIGS. 2A and 2B illustrate the shrinkable or burstable microspheres 206 as spheres or microspheres, it is contemplated by this disclosure that the shrinkable or burstable microspheres 206 can be substantially shaped as ovoids, ellipsoids, cuboids or other polyhedrons, or a combination thereof.

The shrinkable and/or burstable microspheres 206 can be dispersed or otherwise distributed within the composite base material 202 along with the energy absorbing constituent 204. The composite base material 202 can make up the bulk of the first composite material 200. The composite base material 202 can serve as a matrix for holding or carrying the shrinkable and/or burstable microspheres 206 and the energy absorbing constituent 204.

In some embodiments, the energy absorbing constituent 204 can be an energy absorbing colorant. In certain embodiments, the energy absorbing colorant can be an energy absorbing dye. For example, the energy absorbing dye can be an azo dye. In some embodiments, the azo dye can be a red azo dye such as Disperse Red 1 dye. In other embodiments, the azo dye can be an orange azo dye such as Disperse Orange dye (e.g., Disperse Orange 1), a yellow azo dye such as Disperse Yellow dye (e.g., Disperse Yellow 1), a blue azo dye such as Disperse Blue dye (e.g., Disperse Blue 1), or a combination thereof.

In additional embodiments, the energy absorbing colorant can be or comprise a pigment. For example, the energy absorbing colorant can be or comprise graphitized carbon black as the pigment.

When the energy absorbing constituent 204 is an energy absorbing colorant, such as a dye or graphitized carbon, the color of at least part of the first composite material 200 can take on the color of the energy absorbing colorant. For example, when the energy absorbing constituent 204 is an azo dye such as Disperse Red 1 having a red color, at least a portion of the first composite material 200 comprising the energy absorbing constituent 204 can be colored red. Moreover, when the energy absorbing constituent 204 is graphitized carbon having a black color, at least a portion of the first composite material 200 comprising the energy absorbing constituent 204 can be colored black.

The energy absorbing constituent 204 (e.g., azo dye, graphitized carbon black, or a combination thereof) can absorb or capture an external energy (e.g., light energy or, more specifically, laser light) applied or directed at the first composite material 200. The energy absorbing constituent 204 can absorb or capture the external energy and then transform or transfer the energy into thermal energy or heat to the shrinkable and/or burstable microspheres 206.

The color of the energy absorbing colorant can be visually perceptible to a clinician or another medical professional when at least part of the IOL 100 is made of the first composite material 200 comprising the energy absorbing colorant. The color of the energy absorbing colorant can be visually perceptible to a clinician or another medical professional when the IOL 100 is implanted within an eye of a patient. For example, the first composite material 200 can comprise Disperse Red 1 serving as the energy absorbing colorant. In this example, at least part of the IOL 100 can appear red to the clinician or another medical professional when the IOL 100 is implanted within the eye of a patient. The color of the energy absorbing colorant can allow the clinician or another medical professional to detect or determine the location or position of the first composite material 200 within the IOL 100. The color of the energy absorbing colorant can also allow the clinician or another medical professional to determine where to direct the laser light 125 or stimulus to adjust the IOL 100.

FIG. 2B illustrates that the shrinkable or burstable microspheres 206 can comprise an inner phase 208 and one or more vacuum voids 210 contained within a thermoplastic shell 212. The shrinkable microspheres 206 can be configured to shrink or contract in size such that a diameter 214 of at least one of the microspheres can decrease by about one-half of the original diameter.

For example, the shrinkable microspheres 206 can initially be made with a diameter 214 of between about 50 μm and 100 μm. In response to an external energy applied or directed at the first composite material 200 or in response to energy transferred or transmitted to the shrinkable microspheres 206, the diameter 214 of the shrinkable microspheres 206 can decrease to between about 25 μm and 50 μm.

The volume of at least one of the shrinkable microspheres 206 can be configured to decrease by about ten times in response to the external energy applied or directed at the first composite material 200.

The inner phase 208 can be a fluid capable of undergoing one or more phase changes. In some embodiments, the inner phase 208 can be configured to undergo a phase change from a vapor into a liquid phase at a temperature below a boiling point of the inner phase 208. When the inner phase 208 is encapsulated within the thermoplastic shell 212, the one or more vacuum voids 210 can be formed when the inner phase 208 condenses into the liquid phase within the thermoplastic shell 212.

In one embodiment, the inner phase 208 can be or comprise water. In this embodiment, the vacuum voids 210 can be formed when the water vapor within the thermoplastic shell 212 condenses into liquid water.

In other embodiments, the inner phase 208 can be or comprise ethylene glycol (which has a higher boiling point than water). In further embodiments, the inner phase 208 can be or comprise a silicone-based fluid such as certain cyclic siloxanes (e.g., hexamethylcyclotrisiloxane). In additional embodiments, the inner phase 208 can be or comprise polydimethylsiloxane (PDMS) oligomers or certain types of hydrofluoroethers.

As previously discussed, the thermoplastic shell 212 can begin to soften and flow as thermal energy is transferred or transmitted to the shrinkable microspheres 206 from the energy absorbing constituent 204 (see, e.g., FIG. 2A). When the external energy is laser light 125, the energy absorbing constituent 204 can absorb or capture the laser light 125 directed at the first composite material 200 and transform the light energy into thermal energy or heat.

As shown in FIG. 2B, the thermoplastic shell 212 of the shrinkable microspheres 206 can be configured to soften or begin to flow at a temperature above a glass transition temperature ($Tg_{shell}$) of the thermoplastic shell 212. The thermoplastic shell 212 can also begin to thin out at a temperature above a glass transition temperature of the thermoplastic shell 212.

In some embodiments, the glass transition temperature of the thermoplastic shell 212 can be lower than the boiling point of the inner phase 208. In other embodiments, the glass 13 transition temperature of the thermoplastic shell 212 can be substantially equivalent to or close to the boiling point of the inner phase 208.

When the thermoplastic shell 212 is softened or thinned, the thermoplastic shell 212 can collapse and decrease in size due to the external pressure surrounding the thermoplastic shell 212 as well as due to the vacuum within the thermoplastic shell 212.

In some embodiments, at least some of these microspheres 206 can also be configured to burst as the thermoplastic shell 212 disintegrates or ruptures in response to the external energy directed at the first composite material 200. In these embodiments, the inner phase 208 of the burstable microspheres 206 can be dissolved into the surrounding haptic material or silicone oil.

In some embodiments, the thermoplastic shell 212 can be or is made in part of polyacrylonitrile. In some embodiments, the thermoplastic shell 212 can be or is made in part of polystyrene. In further embodiments, the thermoplastic shell 212 can be or is made in part of poly(methyl methacrylate). The thermoplastic shell 212 can also comprise a photoinitiator (e.g., a UV initiator). For example, the photoinitiator can be Omnirad 2022 (bis(2,4,6-trimethylbenzoyl)phenyl-phosphineoxide/2-hydroxy-2-methyl-1-phenyl-propan-1-one). The thermoplastic shell 212 can be formed when monomers of the shell material, along with the photoinitiator, are curved via UV curing As further depicted in FIG. 2B, in the case of the shrinkable microspheres 206, the thermoplastic shell 212 can re-form in its hardened state or become glassy once again when the temperature is below a glass transition temperature of the thermoplastic shell 212 (i.e., when the external energy is no longer directed at the first composite material 200). Moreover, as shown in FIG. 2B, the diameter 214 of the shrinkable microspheres 206 can be reduced when the thermoplastic shell 212 re-forms around the inner phase 208 in the liquid phase and the space formerly occupied by the one or more vacuum voids 210 is displaced.

The change (e.g., decrease in volume) undertaken by the shrinkable microspheres 206 can be a persistent or a substantially permanent change. A persistent or substantially permanent change can mean that the shrinkable microspheres 206 do not substantially revert back to its original shape or size after the change (e.g., after the decrease in volume) has occurred. As a result, any change in the size or volume of the first composite material 200 caused by a change in the size or volume of the shrinkable microspheres 206 is also persistent or substantially permanent.

One technical problem faced by the applicants is how to engineer a shrinkable material that could be used in an IOL 100, is safe for the patient when the IOL 100 is implanted within an eye of the patient, and that would be responsive to an external energy directed at the shrinkable material. One technical solution discovered and developed by the applicants is the first composite material 200 disclosed herein comprising shrinkable and/or burstable microspheres 206 having vacuum voids 210 and a phase-changeable inner phase 208 encapsulated by a thermoplastic shell 212. As will be discussed in more detail in later sections, the shrinkable and/or burstable microspheres 206 are formed initially when the inner phase 208 is in its vaporous phase and the vacuum void(s) 210 are formed when the inner phase 208 condenses into its liquid phase within the thermoplastic shell 212.

FIG. 2C is a graphic representation of one embodiment of a second composite material 201 comprising the composite base material 202, the energy absorbing constituent 204, and a plurality of expandable components 207. As previously discussed, one or more portions of each of the haptics 104 can be made of the second composite material 201 such as the lumen filler 126.

The composite base material 202 can be comprised of hydrophobic acrylic materials. For example, the composite base material 202 can be comprised of phenylethyl acrylate (PEA), a phenylethyl methacrylate (PEMA), or a combination thereof.

In one example embodiment, the composite base material 202 can comprise a methacrylate-functional or methacrylic-functional cross-linkable polymer and reactive acrylic monomer diluents including lauryl methacrylate (n-dodecyl methacrylate or SR313) and ADMA. By controlling the amount of lauryl methacrylate (SR313) to ADMA, the overall corresponding hardness (i.e., more ADMA) or softness (i.e., more SR313) of the cured composite material 200 can be controlled. The methacrylate-functional or methacrylic-functional cross-linkable polymer can be made using the cross-linkable polymer precursor formulation.

The cross-linkable polymer precursor formulation can comprise the same copolymer blend used to make the optic portion 102 and the haptics 104.

The copolymer blend can comprise an alkyl acrylate or methacrylate (e.g., n-butyl acrylate), a fluoro-alkyl (meth) acrylate (e.g., trifluoroethyl methacrylate), and a phenyl-alkyl acrylate (e.g., phenylethyl acrylate). For example, the copolymer blend can comprise n-butyl acrylate in the amount of about 41% to about 45% (wt %), trifluoroethyl methacrylate in the amount of about 20% to about 24% (wt %), and phenylethyl acrylate in the amount of about 28% to about 32% (wt %). The cross-linkable polymer precursor formulation can comprise or be made in part of the copolymer blend, a hydroxyl-functional acrylic monomer (e.g., HEA), and a photoinitiator (e.g., Darocur 4265 or a 50/50 blend of diphenyl(2,4,6-trimethylbenzoyl)-phosphine oxide and 2-hydroxy2-methylpropiophenone).

The composite base material 202 can comprise the methacrylate-functional or methacrylic-functional cross-linkable polymer (as discussed above) in the amount of about 50% to about 65% (e.g., about 55% to about 60%) (wt %), the reactive acrylic monomer diluent lauryl methacrylate (SR313) in the amount of about 32% to about 38% (e.g., about 32.70%) (wt %), the reactive acrylic monomer diluent adamantly methacrylate (ADMA) in the amount of about 5% to about 9% (e.g., about 7.30%) (wt %).

Table 2 below provides an example formulation for the second composite material 201:

TABLE 2

| FORMULATION OF SECOND COMPOSITE MATERIAL (WT %) | |
| --- | --- |
| Cross-linkable polymer (in two steps from precursor formulation, as described above) | 1.47% 2-hydroxyethyl acrylate (HEA)<br>1.96% Darocur 4265 (photoinitiator)<br>43.49% n-butylacrylate (nBA)<br>30.21% 2-phenylethylacrylate (PEA)<br>22.87% 2,2,2-trifluoroethylmethacrylate (TFEMA) |
| Composite base material | 60.00% cross-linkable polymer<br>32.70% lauryl methacrylate (SR313)<br>7.30% 1-adamantyl methacrylate (ADMA) |

TABLE 2-continued

| FORMULATION OF SECOND COMPOSITE MATERIAL (WT %) | |
| --- | --- |
| Composite base material with red energy absorbing colorant | 99.50% composite base material 0.50% Disperse Red 1 dye |
| Composite base material with black energy absorbing colorant | 99.95% composite base material 0.05% graphitized mesoporous carbon black |
| Final formulation of second composite material | 87.70% composite base material with red or black energy absorbing colorant 10.00% expandable microspheres 1.00% Luperox peroxide (thermal initiator) 1.30% Omnirad 2022 |

In some embodiments, the second composite material 201 can be made in several operations. The first operation can comprise preparing an uncolored composite base material 202. The second operation can comprise mixing the composite base material 202 with the energy absorbing constituent 204, the expandable components 207, and initiators such as one or more photoinitiators, thermal initiators, or a combination thereof. The third operation can comprise placing the uncured second composite material 201 into a desired location within the haptics 104 (e.g., in proximity to the channel 148), and curing the second composite material in place.

As previously discussed, the second composite material 201 can be positioned radially offset from the first composite material 200 within the haptic 104.

The uncolored composite base material 202 can be mixed with an energy absorbing constituent 204 such as a dye (e.g., Disperse Red 1 dye) or pigment (graphitized carbon black). The energy absorbing constituent 204 will be discussed in more detail below.

In some embodiments, the expandable components 207 can make up about 5.0% to about 15.0% by weight of a final formulation of the second composite material 201. More specifically, the expandable components 207 can make up about 8.0% to about 12.0% (e.g., about 10.0%) by weight of a final formulation (see Table 2) of the second composite material 201. In these and other embodiments, the energy absorbing constituent 204 can make up about 0.044% to about 0.44% (or about 0.55%) by weight of the final formulation of the composite material 200.

The photoinitiator can be Omnirad 2022 (bis(2,4,6-trimethylbenzoyl)phenyl-phosphineoxide/2-hydroxy-2-methyl-1-phenyl-propan-1-one). The photoinitiator can make up about 1.30% by weight of a final formulation of the composite material 200 (see, e.g., Table 2). In addition, the composite material 200 can also comprise a thermal initiator. The thermal initiator can make up about 1.00% by weight of a final formulation of the composite material 200 (see, e.g., Table 2). In some embodiments, the thermal initiator can be a dialkyl peroxide such as Luperox® peroxide. In other embodiments, the thermal initiator can be Perkadox.

In some embodiments, the energy absorbing constituent 204 can absorb the external energy (e.g., laser energy) and convert the energy to heat. The heat energy can be conducted to the expandable components 207 (e.g., via the composite base material 202) to expand the expandable components 207.

Figure 2D:
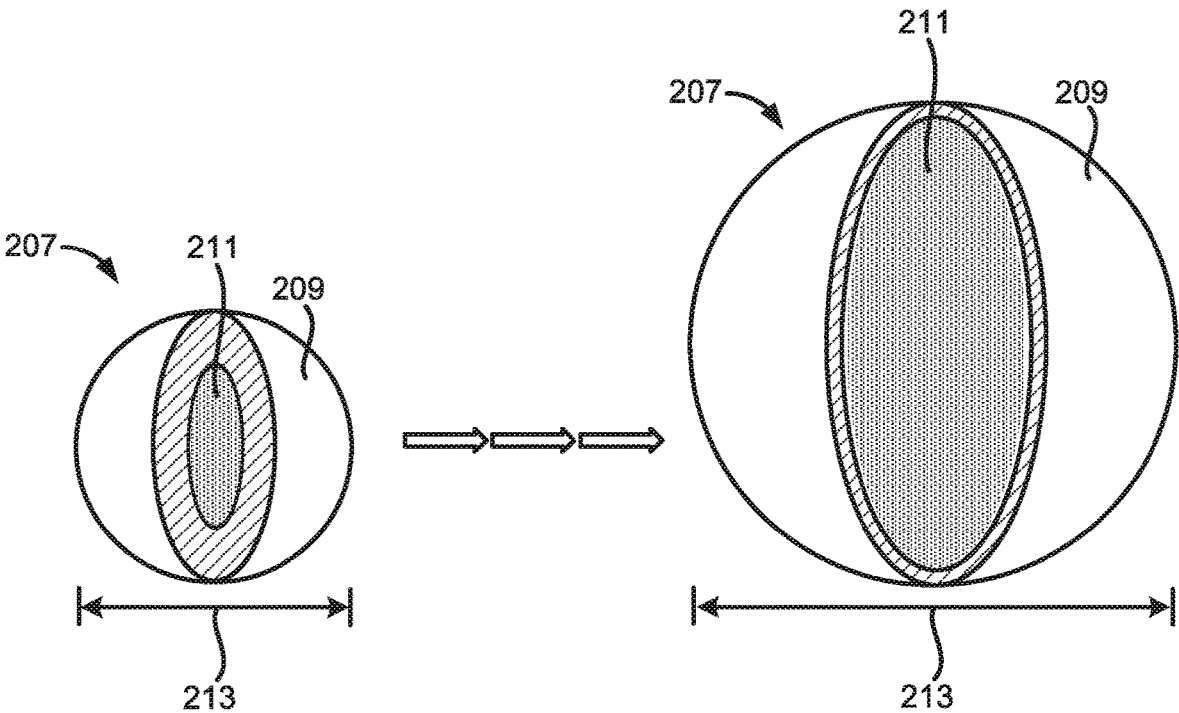
FIG. 2D is a pictorial representation of an expandable component of the second composite material increasing in size in response to the external energy applied to the second composite material.

FIG. 2D illustrates that the expandable components 207 can be expandable microspheres comprising an expandable thermoplastic shell 209 and a blowing agent 211 contained within the expandable thermoplastic shell 209. The expandable microspheres can be configured to expand such that a diameter 213 of at least one of the microspheres can increase by about 2× the original diameter. In other embodiments, the expandable microspheres can be configured to expand such that the diameter 213 of at least one of the microspheres can increase by about 4× or four times the original diameter. In further embodiments, the expandable microspheres can be configured to expand such that the diameter 213 of at least one of the microspheres can increase between about 2× to about 4× (or about 3.5×) the original diameter. For example, the expandable microspheres can have a diameter 213 of about 12 μm at the outset. In response to an external energy applied or directed at the second composite material 201, the diameter 213 of the expandable microspheres can increase to about 40 μm.

The volume of at least one of the expandable microspheres can be configured to expand between about ten times (10×) to about 50 times (50×) in response to the external energy applied or directed at the second composite material 201.

In some embodiments, the blowing agent 211 can be an expandable fluid, such as an expandable gas. More specifically, the blowing agent 211 can be a branched-chain hydrocarbon. For example, the blowing agent 211 can be isopentane. In other embodiments, the blowing agent 211 can be or comprise cyclopentane, pentane, or a mixture of cyclopentane, pentane, and isopentane.

The expandable components 207 can comprise differing amounts of the blowing agent 211. For example, some expandable components 207 can comprise more or a greater amount of the blowing agent 211 (e.g., more expandable gas) to allow such expandable components 207 to expand more, resulting in greater expansion of the second composite material 201 comprising such expandable components 207.

FIG. 2D illustrates that each of the expandable components 207 can comprise a thermoplastic shell 209. FIG. 2D also illustrates that a thickness of the thermoplastic shell 209 can change as the expandable component 207 increases in size. More specifically, the thickness of the thermoplastic shell 209 can decrease as the expandable component 207 increases in size. For example, when the expandable components 207 are expandable microspheres, the thickness of the thermoplastic shell 209 (i.e., its thickness in a radial direction) can decrease as the diameter 213 of the expandable microsphere increases.

For example, as previously discussed, at least one of the expandable microspheres can have a diameter 213 of about 12 μm at the outset. In this embodiment, the thermoplastic shell 209 of the expandable microsphere can have a shell thickness of about 2.0 μm. In response to an external energy applied or directed at the second composite material 201, the diameter 213 of the microsphere can increase to about 40 μm (and the volume expand between about 10× and 50×) and the shell thickness of the microsphere can decrease to about 0.1 μm.

Although FIGS. 2C and 2D illustrate the expandable components 207 as spheres or microspheres, it is contemplated by this disclosure that the expandable components 207 can be substantially shaped as ovoids, ellipsoids, cuboids or other polyhedrons, or a combination thereof.

In some embodiments, the thermoplastic shell 209 can be made in part of nitriles or acrylonitrile copolymers. For example, the thermoplastic shell 209 can be made in part of acrylonitrile, styrene, butadiene, methyl acrylate, or a combination thereof.

As previously discussed, the expandable components 207 can make up between about 8.0% to about 12% by weight of a final formulation of the second composite material 201. The expandable components 207 can make up about 10% by weight of a final formulation of the second composite material 201.

The expandable components 207 can be dispersed or otherwise distributed within the composite base material 202 making up the bulk of the second composite material 201. The composite base material 202 can serve as a matrix for holding or carrying the expandable components 207. The second composite material 201 can expand in response to an expansion of the expandable components 207 (e.g., the expandable microspheres). For example, a volume of the second composite material 201 can increase in response to the expansion of the expandable components 207.

The second composite material 201 also comprises an energy absorbing constituent 204. In some embodiments, the energy absorbing constituent 204 can be an energy absorbing colorant.

In certain embodiments, the energy absorbing colorant can be an energy absorbing dye. For example, the energy absorbing dye can be an azo dye. In some embodiments, the azo dye 19 can be a red azo dye such as Disperse Red 1 dye. In other embodiments, the azo dye can be an orange azo dye such as Disperse Orange dye (e.g., Disperse Orange 1), a yellow azo dye such as Disperse Yellow dye (e.g., Disperse Yellow 1), a blue azo dye such as Disperse Blue dye (e.g., Disperse Blue 1), or a combination thereof.

In additional embodiments, the energy absorbing colorant can be or comprise a pigment. For example, the energy absorbing colorant can be or comprise graphitized carbon black as the pigment.

Similar to the expandable components 207, the energy absorbing constituent 204 can be dispersed or otherwise distributed within the composite base material 202 making up the bulk of the second composite material 201. The composite base material 202 can serve as a matrix for holding or carrying the expandable components 207 and the energy absorbing constituent 204.

The energy absorbing constituent 204 can make up between about 0.025% to about 1.0% (or, more specifically, about 0.045% to about 0.45%) by weight of a final formulation of the second composite material 201. For example, when the energy absorbing constituent 204 is a dye (e.g., an azo dye such as Disperse Red 1), the energy absorbing constituent 204 can make up about between about 0.45% to about 1.0% by weight of a final formulation of the second composite material 201. When the energy absorbing constituent 204 is graphitized carbon black or other types of pigments, the energy absorbing constituent 204 can make up about 0.025% to about 0.045% by weight of a final formulation of the second composite material 201.

The energy absorbing constituent 204 (e.g., azo dye, graphitized carbon black, or a combination thereof) can absorb or capture an external energy (e.g., light energy or, more specifically, laser light) applied or directed at the second composite material 201. The energy absorbing constituent 204 can absorb or capture the external energy and then transform or transfer the energy into thermal energy or heat to the expandable components 207.

The thermoplastic shell 209 can soften and begin to flow as thermal energy is transferred or transmitted to the expandable components 207. The thermoplastic shell 209 of the expandable components 207 can then begin to thin or reduce in thickness in response to the thermal energy transferred or transmitted to the expandable components 207. As the thermoplastic shell 209 begins to soften and reduce in thickness, the blowing agent 211 within the expandable components 207 can expand. The blowing agent 211 can also expand in response to the thermal energy or heat transferred or transmitted to the expandable components 207. Expansion of the blowing agents 211 can cause the expandable components 207 (e.g., the thermoplastic microspheres) to expand or increase in volume. This ultimately causes the second composite material 201 to expand or increase in volume.

The second composite material 201 can expand or increase in size in an isotropic manner such that the second composite material 201 expands in all directions. Such isotropic expansion can be harnessed to produce expansion or material displacement in specific directions by placing or positioning the second composite material 201 at specific locations within the haptic(s) 104 of the IOL 100.

As previously discussed, the external energy can be laser light 125 and the energy absorbing constituent 204 can absorb or capture the laser light 125 directed at the second composite material 201 and transform or transfer the light energy into thermal energy or heat to the expandable components 207. The blowing agent 211 within the expandable components 207 can expand or become energized in response to the thermal energy or heat. The expandable components 207 and, ultimately, the second composite material 201 can expand or increase in volume in response to this light energy directed at the second composite material 201.

The shape change (e.g., increase in volume) undertaken by the expandable components 207 can be a persistent or a substantially permanent change. A persistent or substantially permanent change can mean that the expandable components 207 do not substantially revert back to its original shape or size after the shape change (e.g., after an increase in volume) has occurred. As a result, any change in the size or volume of the second composite material 201 caused by a change in the size or volume of the expandable components 207 is also persistent or substantially permanent. As will be discussed in more detail in the following sections, this means that any structural changes made to the IOL 100 as a result of external energy or stimulus applied or otherwise directed at the second composite material 201 embedded or integrated within the IOL 100 can persist or remain substantially permanent.

The thermoplastic shells 209 of the expandable components 207 can harden, once again, when the external energy is no longer directed or applied to the second composite material 201. For example, the thermoplastic shells 209 may harden, once again, when the temperature within a vicinity of the expandable components 207 falls below a certain threshold. For example, the thermoplastic shells 209 of the expandable microspheres can harden when light energy is no longer directed at the second composite material 201. After the thermoplastic shells 209 harden, the expandable components 207 are locked into their new size and expanded configuration.

When the energy absorbing constituent 204 is an energy absorbing colorant, such as a dye or graphitized carbon, the color of at least part of the second composite material 201 can take on the color of the energy absorbing colorant. For example, when the energy absorbing constituent 204 is an azo dye such as Disperse Red 1 having a red color, at least a portion of the second composite material 201 comprising the energy absorbing constituent 204 can be colored red. Moreover, when the energy absorbing constituent 204 is graphitized carbon having a black color, at least a portion of the second composite material 201 comprising the energy absorbing constituent 204 can be colored black. Although two colors (e.g., red and black) are mentioned in this disclosure, it is contemplated by this disclosure and it should be understood by one of ordinary skill in the art that energy absorbing colorant of other types of colors can also be used such as energy absorbing yellow, orange, or blue dyes or materials.

The color of the energy absorbing colorant can be visually perceptible to a clinician or another medical professional when at least part of the IOL 100 is made of the second composite material 201 comprising the energy absorbing colorant. The color of the energy absorbing colorant can be visually perceptible to a clinician or another medical professional when the IOL 100 is implanted within an eye of a patient. For example, the second composite material 201 can comprise Disperse Red 1 serving as the energy absorbing colorant. In this example, at least part of the IOL 100 can appear red to the clinician or another medical professional when the IOL 100 is implanted within the eye of a patient. The color of the energy absorbing colorant can allow the clinician or another medical professional to detect or determine the location or position of the second composite material 201 within the IOL 100. The color of the energy absorbing colorant can also allow the clinician or another medical professional to determine where to direct the laser light 125 or stimulus to adjust the IOL 100.

In some embodiments, the different energy absorbing colorants can be used in the same IOL 100 to help distinguish between the first composite material 200 and the second composite material 201. For example, the first composite material 200 can comprise a red dye (e.g., Disperse Red 1) serving as the energy absorbing colorant and the second composite material 201 can comprise a black pigment (e.g., graphitized carbon) serving as the energy absorbing colorant. In this example, the part of the IOL 100 comprising the first composite material 200 can appear red to the clinician or another medical professional and the part of the IOL 100 made of the second composite material 201 can appear black to the clinician or another medical professional when the IOL 100 is implanted within the eye of a patient. This color difference can allow the clinician or another medical professional to differentiate between the first composite material 200 and the second composite material 201 within the IOL 100. More specifically, this color difference can guide the clinician or another medical professional in determining where to direct the laser light 125 when either a negative optical power change or a positive optical power change is desired.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. An intraocular lens, comprising:
an optic portion;
one or more haptics coupled to the optic portion;
    wherein at least one of the haptics comprises a composite material, wherein the composite material comprises an energy absorbing constituent and a plurality of at least one of shrinkable microspheres and burstable microspheres, and
    wherein a base power of the optic portion is configured to change in response to an external energy directed at the composite material.

2. The intraocular lens of claim 1, wherein each of the shrinkable microspheres and burstable microspheres comprises an inner phase and one or more vacuum voids contained within a thermoplastic shell.

3. The intraocular lens of claim 2, wherein the inner phase is configured to undergo a phase change from a vapor into a liquid phase at a temperature below a boiling point of the inner phase, and wherein the vacuum voids are formed when the inner phase condenses into the liquid phase within the thermoplastic shell.

4. The intraocular lens of claim 3, wherein the inner phase is water.

5. The intraocular lens of claim 3, wherein the inner phase is ethylene glycol.

6. The intraocular lens of claim 2, wherein the thermoplastic shell is made in part of polyacrylonitrile.

7. The intraocular lens of claim 2, wherein the thermoplastic shell is made in part of polystyrene.

8. The intraocular lens of claim 2, wherein the thermoplastic shell is made in part of poly(methyl methacrylate).

9. The intraocular lens of claim 2, wherein the thermoplastic shell is configured to soften at a temperature above a glass transition temperature of the thermoplastic shell.

10. The intraocular lens of claim 9, wherein the thermoplastic shell is configured to soften and collapse in response to the external energy directed at the composite material and re-form around the inner phase.

11. The intraocular lens of claim 2, wherein a diameter of at least one of the shrinkable microspheres is configured to decrease by about one-half in response to the external energy directed at the composite material.

12. The intraocular lens of claim 1, wherein the at least one of the shrinkable microspheres and the burstable microspheres comprises between about 5% to about 25% by weight of the composite material.

13. The intraocular lens of claim 1, wherein the energy absorbing constituent is an energy absorbing colorant.

14. The intraocular lens of claim 13, wherein the energy absorbing colorant is a dye.

15. The intraocular lens of claim 13, wherein the energy absorbing colorant is a pigment.

16. The intraocular lens of claim 1, wherein at least one of the optic portion and the one or more haptics are made in part of a cross-linked copolymer comprising a copolymer blend, and wherein the composite material is made in part of the copolymer blend.

17. The intraocular lens of claim 1, wherein the external energy is light energy.

18. A method of adjusting an intraocular lens, comprising:
adjusting a base power of the intraocular lens by directing an external energy at a composite material within at least one haptic of the intraocular lens,
    wherein the composite material comprises an energy absorbing constituent and a plurality of at least one of shrinkable microspheres and burstable microspheres.

19. An intraocular lens, comprising:
an optic portion; and
at least one haptic coupled to the optic portion,
    wherein the at least one haptic comprises a first composite material, wherein the first composite material comprises an energy absorbing constituent and a plurality of at least one of shrinkable microspheres and burstable microspheres,
    wherein a portion of the at least one haptic is made in part of a second composite material comprising the energy absorbing constituent and a plurality of expandable microspheres,
    wherein a base power of the optic portion is configured to decrease in response to an external energy directed at the first composite material, and
    wherein the base power of the optic portion is configured to increase in response to the external energy directed at the second composite material.

20. A size-adjustable ophthalmic material, comprising:
an energy absorbing constituent; and
a plurality of at least one of shrinkable microspheres and burstable microspheres, and wherein a size of the ophthalmic material is configured to change in response to an external energy directed at the ophthalmic material.

* * * * *